United States Patent
Shimogami et al.

(10) Patent No.: US 7,909,779 B2
(45) Date of Patent: Mar. 22, 2011

(54) CATHETER AND METHOD OF PRODUCING THE SAME

(75) Inventors: Manabu Shimogami, Nagoya (JP); Shinichi Goto, Nagoya (JP); Masaaki Nihonmatsu, Nagoya (JP)

(73) Assignee: Asahi Intecc Co., Ltd., Nagoya (JP)

( * ) Notice: Subject to any disclaimer, the term of this patent is extended or adjusted under 35 U.S.C. 154(b) by 606 days.

(21) Appl. No.: 11/303,414

(22) Filed: Dec. 16, 2005

(65) Prior Publication Data

US 2006/0178653 A1 Aug. 10, 2006

(30) Foreign Application Priority Data

Dec. 21, 2004 (JP) ................................. 2004-369969

(51) Int. Cl.
*A61B 5/00* (2006.01)
(52) U.S. Cl. ........... 600/585; 604/526; 604/523; 72/135
(58) Field of Classification Search .................. 600/585, 600/433
See application file for complete search history.

(56) References Cited

U.S. PATENT DOCUMENTS

| | | | |
|---|---|---|---|
| 3,727,902 A * | 4/1973 | Burckhardt et al. ....... | 267/166.1 |
| 3,815,608 A | 6/1974 | Spinosa et al. | |
| 4,080,706 A * | 3/1978 | Heilman et al. ................ | 29/592 |
| 4,654,024 A | 3/1987 | Crittenden et al. | |
| 4,810,231 A * | 3/1989 | Weissenberger et al. .... | 464/68.4 |
| 4,842,579 A | 6/1989 | Shiber | |
| 4,857,045 A | 8/1989 | Rydell | |
| 4,883,458 A | 11/1989 | Shiber | |
| 4,886,490 A | 12/1989 | Shiber | |
| 4,898,575 A | 2/1990 | Fischell et al. | |
| 4,909,781 A | 3/1990 | Husted | |
| 5,026,384 A | 6/1991 | Farr et al. | |
| 5,041,082 A | 8/1991 | Shiber | |
| 5,078,723 A | 1/1992 | Dance et al. | |
| 5,127,917 A | 7/1992 | Niederhauser et al. | |
| 5,131,406 A | 7/1992 | Kaltenbach | |
| 5,147,317 A | 9/1992 | Shank et al. | |
| 5,201,750 A | 4/1993 | Hocherl et al. | |
| 5,259,393 A * | 11/1993 | Corso et al. .................... | 600/585 |
| 5,314,438 A | 5/1994 | Shturman | |
| 5,365,942 A * | 11/1994 | Shank ........................... | 600/585 |
| 5,402,799 A * | 4/1995 | Colon et al. .................. | 600/585 |
| 5,571,122 A | 11/1996 | Kelly et al. | |
| 5,665,098 A | 9/1997 | Kelly et al. | |
| 5,742,019 A | 4/1998 | Radisch, Jr. | |
| 5,800,450 A | 9/1998 | Lary et al. | |

(Continued)

FOREIGN PATENT DOCUMENTS

EP 0 611 073 A1 8/1994
(Continued)

*Primary Examiner* — Max Hindenburg
*Assistant Examiner* — Renee Danega
(74) *Attorney, Agent, or Firm* — Knobbe, Martens, Olson & Bear, LLP

(57) ABSTRACT

A catheter body includes a coil body (10) which is formed by winding or stranding metal wires (12) and having a distal portion (16) and a proximal portion. The distance between coils (12) adjacent to each other in the distal portion (16) is greater than the distance between coils (12) adjacent to each other in the proximal portion (18 or 14). The pitch in the distal portion (16) of the coil body (10) is substantially or nearly the same as the pitch in the proximal portion (18 or 14).

15 Claims, 12 Drawing Sheets

U.S. PATENT DOCUMENTS

| | | | |
|---|---|---|---|
| 6,348,041 B1 * | 2/2002 | Klint | 600/585 |
| 6,589,227 B2 * | 7/2003 | Sønderskov Klint | 604/524 |
| 6,648,837 B2 * | 11/2003 | Kato et al. | 600/585 |
| 6,881,194 B2 * | 4/2005 | Miyata et al. | 600/585 |
| 2001/0041881 A1 * | 11/2001 | Sarge et al. | 604/525 |
| 2001/0044633 A1 | 11/2001 | Klint | |
| 2002/0095102 A1 * | 7/2002 | Winters | 600/585 |
| 2003/0216761 A1 | 11/2003 | Shiber | |
| 2004/0010243 A1 | 1/2004 | Klint | |
| 2004/0082879 A1 | 4/2004 | Klint | |
| 2004/0116833 A1 * | 6/2004 | Kato et al. | 600/585 |
| 2004/0249277 A1 | 12/2004 | Kato et al. | |
| 2005/0022572 A1 | 2/2005 | Kato et al. | |
| 2005/0027309 A1 | 2/2005 | Shiber | |
| 2005/0119615 A1 * | 6/2005 | Noriega et al. | 604/95.04 |
| 2005/0154400 A1 | 7/2005 | Kato et al. | |
| 2005/0222585 A1 | 10/2005 | Miyata et al. | |

FOREIGN PATENT DOCUMENTS

| | | |
|---|---|---|
| EP | 0 850 656 A1 | 7/1998 |
| EP | 1 243 283 A2 | 9/2002 |
| EP | 1 321 162 A1 | 6/2003 |
| GB | 1 208 639 A | 10/1970 |
| JP | U 02-42285 | 11/1990 |
| JP | 06-197903 | 7/1994 |
| JP | 07-227429 | 8/1995 |
| JP | 2002-315835 A | 10/2002 |
| JP | 2003-520651 A | 7/2003 |
| WO | WO 2004/012804 A2 | 2/2004 |

* cited by examiner

CATHETER AND METHOD OF PRODUCING THE SAME

BACKGROUND OF THE INVENTION

1. Field of the Invention

The present invention relates to an improved catheter having a catheter body comprising a coil body, as well as a method of producing such catheter in a favorable manner.

2. Description of the Related Art

Catheters have been known as medical apparatuses that are used via insertion into blood vessels, gastrointestinal tracts, urinary tracts and other tubular organs and tissues of humans. As one type of these catheters, those having its main body, or part inserted into the human body, comprising a coil body formed by winding or stranding long, thin round metal wires are known (such as the one disclosed in Japanese Patent Laid-open Publication No. 2004-242973). For example, these catheters are favorably used in procedures that are performed to dilate an occluded area in a blood vessel.

Specifically, when performing a procedure using one of these catheters having a coil body as the catheter body, generally a guide wire is inserted into the occluded area. Then, the coil body is guided by the guide wire into the occluded area. The coil body dilates the occluded area and forms a somewhat large channel in the occluded area. Next, a relatively small balloon catheter is inserted into the aforementioned channel, after which the balloon is inflated to expand the occluded area further. After this process, a larger balloon catheter may be inserted and inflated, if necessary, to expand the occluded area further. This ensures a sufficient blood flow through the applicable blood vessel.

In these procedures, the aforementioned catheters exhibits excellent operation performance in blood vessels based on the sufficient flexibility and good torque transmissibility of their coil bodies. This is why the bodies of these catheters can be smoothly inserted into blood vessels without damaging the interior walls of the blood vessels. These catheter bodies also allow an occluded area to be dilated in a reliable, easy manner to a sufficient size at which a balloon catheter can be inserted.

SUMMARY OF THE INVENTION

However, conventional catheters of this type generally have a coil body whose outer diameter is around 0.61 mm, which is only slightly larger than the outer diameters of small balloon catheters. Therefore, in order to expand an occluded area in a blood vessel further using a larger balloon catheter, the surgeon had to perform a procedure using a catheter having a conventional coil body, followed by two more procedures using a small balloon catheter and a large balloon catheter. To address this troublesome procedure, the inventors searched for a simpler procedure that could achieve the same effect.

Here, one method that easily comes to one's mind for reducing the operator's burden in these procedures where an occluded area in a blood vessel is dilated, is to increase the outer diameter of the coil body so that insertion of the coil body will create a larger channel in the occluded area of the blood vessel into which a large balloon catheter can be inserted. This eliminates the need to perform a procedure using a small balloon catheter.

In reality, however, the inventors found that increasing the outer diameter of the coil body would present numerous problems. In general, the larger the outer diameter of the coil body, the thicker the metal wires composing the coil body become. For this reason, increasing the outer diameter of the coil body generally reduces the flexibility of the entire coil body. Lower flexibility of the coil body in turn increases the rigidity of the coil body at its distal portion where sufficient flexibility is particularly required. This gives rise to problems, such as the difficulty inserting the coil body smoothly into meandering blood vessels so as not to damage the interior walls of the blood vessels.

If a coil with a larger outer diameter is formed with thinner metal wires to prevent the aforementioned problems, the flexibility of the entire coil increases excessively. In this case, the rigidity of the coil body drops at its proximal portion where an appropriate level of rigidity is required. As a result, torque transmissibility decreases significantly.

Of course, it is also possible to simply increase the outer diameter of the coil body without changing the thickness of its metal wires. In this case, however, the inner diameter of the coil body also increases, and the difference between the inner diameter of the coil body and the outer diameter of the guide wire inserted into the coil body increases invariably. This gives rise to a different set of problems, such as the guiding of the coil body by the guide wire becoming unstable. The problem of unstable guide wire operation also occurs when a coil body with a large outer diameter is created using thin metal wires.

As explained above, it has not been easy to increase the outer diameter of a conventional catheter having a catheter body comprising a coil body, in a manner maintaining good operation performance of the coil body in a procedure in which an occluded area in a blood vessel is dilated.

The present invention was conceived in view of the aforementioned background, and an object of the present invention is to provide an improved structure that pertains to a catheter having a catheter body comprising a coil body, wherein the catheter having this structure can be operated in a simpler manner, without reducing the operation performance of the coil body in any way, in a procedure in which an occluded area in a blood vessel is dilated. Another object of the present invention is to provide a method of producing in a favorable manner the aforementioned catheter offering such excellent characteristics.

In an aspect for achieving one or more of the above objects, the present invention provides a catheter body configured to be inserted into the human body comprising a coil body constituted by coils of at least one wire wound or stranded in the same general direction, said coil body having a distal portion which is configured to be inserted into a target blood vessel, wherein a distance Wd between coils adjacent to each other in the distal portion is greater than a distance Wp between coils adjacent to each other in a portion adjacent to the distal portion toward a proximal end of the coil body. In the above, the "coils" may be referred to as the "wires" even when the coil body is constituted by only one wire wounded or stranded.

The above aspect includes, but is not limited to, the following embodiments:

The coils of the coil body in the distal portion may have a pitch which is substantially or nearly identical to a pitch of the coils of the coil body in the portion adjacent to the distal portion.

The pitch of the coils in the distal portion and in the portion adjacent thereto may be about 1.15 mm to about 2.25 mm. The distance Wd may be about 8% to about 15% of a sum of the distance Wd and a width of one of the adjacent coils. A total of the distance Wd per pitch of the coils in the distal portion may be about 8% to about 15% of the pitch. The distance Wp may be substantially or nearly zero.

The at least one wire may comprise two or more wires constituting the coil body. The two or more wires may be 8 to 12 wires.

The distal portion of the coil body may have a tip-tapered part having an inner diameter and an outer diameter that both decrease toward its tip. The catheter body may further comprise a tip portion affixed to the tip-tapered part of the distal portion of the coil body, wherein the tip portion is made of a radio-opaque material. The distal portion of the coil body may have an outer diameter, the minimum value of which is about 0.6 mm to about 0.8 mm. The distal portion of the coil body may have an outer diameter, the maximum value of which is about 0.85 mm to about 0.90 mm.

The distal portion of the coil body may have an inner diameter, the minimum value of which corresponds to about 5% to about 20% of an outer diameter of a guide wire to be inserted axially movably into the coil body.

The distal portion of the coil body may have a length of about 5 mm to 250 mm.

The distance Wd may be formed by electro-polishing of the distal portion of the coil body without substantially or nearly changing a pith of the coils. The coil body may have reduced stress by heat-treating of the coil body before the electro-polishing. The distal portion of the coil body may have a surface, at least a portion of which is polished by centerless-grinding and has an outer diameter which is smaller than an outer diameter of the portion adjacent to the distal portion. Further, the coil body may be composed of a single layer of the wire(s).

In another aspect for achieving one or more of the above objects, the present invention provides a catheter configured to be inserted into the human body, comprising: the catheter body; a cover tube which covers a proximal portion of the catheter body opposite to the distal portion of the catheter body; and a connector with which the proximal portion of the catheter body is coupled.

In all of the aforesaid aspects and embodiments, any element used in one aspect or embodiment can interchangeably or additionally be used in another aspect or embodiment unless such a replacement or addition is not feasible or causes adverse effect. Further, the present invention can equally be applied to apparatuses and methods.

In still another aspect for achieving one or more of the above objects, the present invention provides a method of producing the catheter body, comprising: (i) winding or stranding the at least one wire in the same general direction to create the coil body having the distal portion and the portion adjacent thereto; and (ii) subjecting the distal portion of the coil body to a polishing treatment to create the distance Wd which is greater than the distance Wp in the portion adjacent thereto. In the above, the polishing treatment may be electro-polishing.

The above aspect includes, but is not limited to, the following embodiments:

The polishing treatment may be electro-polishing. The polishing treatment may continue to form the distance Wd such that a total of the distance Wd per pitch of the coil in the distal portion is about 8% to about 15% of the pitch. In the winding or stranding step, the at least one wire may be wound or stranded at a constant pitch throughout the coil body. The centerless-grinding may continue to set a maximum outer diameter of the distal portion of the coil body at about 0.85 mm to about 0.90 mm.

The method may further comprise heat-treating the coil body prior to electro-polishing to reduce residual stress created in the winding or stranding step.

The method may further comprise centerless-grinding an outer periphery of the distal portion of the coil body prior to the electro-polishing to reduce an outer diameter of the distal portion of the coil body as compared with an outer diameter of the portion adjacent to the distal portion.

The method may further comprise swaging a tip portion of the distal portion of the coil body prior to the electro-polishing to reduce an outer diameter of the tip portion as compared with an outer diameter of the remaining portions of the coil body.

In the winding or stranding step, multiple wires as the at least one wire may be wound or stranded at a constant pitch.

For purposes of summarizing the invention and the advantages achieved over the related art, certain objects and advantages of the invention have been described above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Further aspects, features and advantages of this invention will become apparent from the detailed description of the preferred embodiments which follow.

BRIEF DESCRIPTION OF THE DRAWINGS

These and other features of this invention will now be described with reference to the drawings of preferred embodiments which are intended to illustrate and not to limit the invention.

Figure 1:
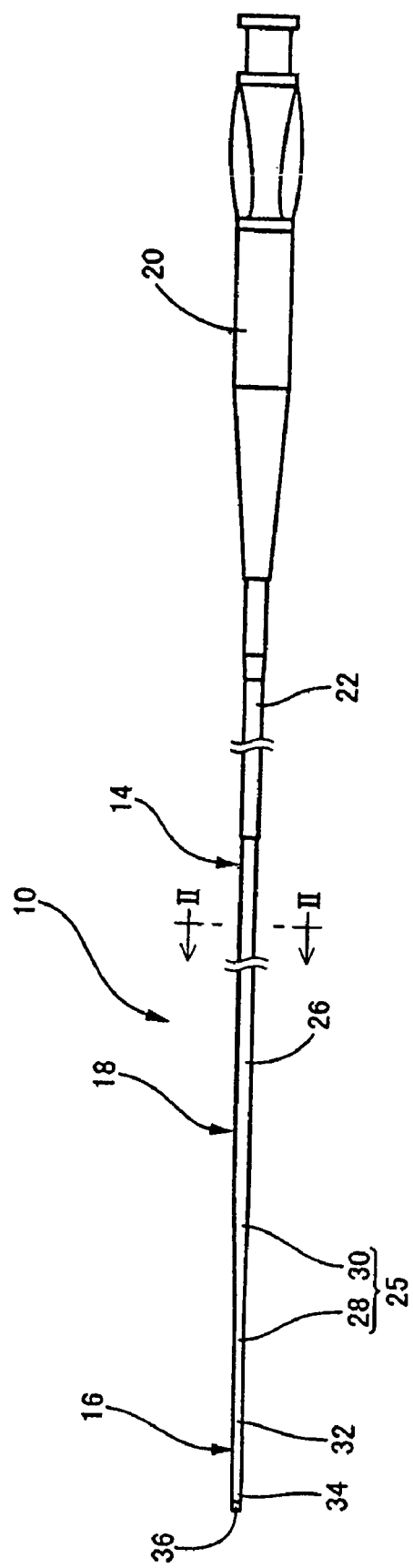
FIG. 1 is an explanatory diagram showing a front view of an example of catheter having a structure according to at least one embodiment of the present invention.

Description of the Symbols is as follows: 10: Coil body; 12: Wire; 14: Proximal portion; 16: Distal portion; 24: Guide wire; 32: Tip cylinder part; 34: Tip tapered part; 38: Gap; 54: Blood vessel; 56: Occluded area.

DETAILED DESCRIPTION OF THE PREFERRED EMBODIMENT

The present invention will be explained with respect to preferred embodiments. However, the preferred embodiments are not intended to limit the present invention, but include the following:

<1> A catheter including a catheter body of a specified length to be inserted into the human body; wherein the catheter body comprises a coil body formed by winding or stranding metal wires and having a distal portion and a proximal portion; and wherein the pitch in the distal portion of the coil body is substantially or nearly the same as the pitch in the proximal portion, while the distance between each pair of the metal wires running adjacent to each other in the distal portion is larger than the distance between each pair of the metal wires running adjacent to each other in the proximal portion.

<2> A catheter described in <1> above, wherein the coil body is electro-polished in the distal portion in order to polish the surface of the metal wires in the distal portion and create a gap between each pair of adjacent metal wires in the distal portion, so that the distance between each pair of the metal wires running adjacent to each other in the distal portion becomes larger that the distance between each pair of the metal wires running adjacent to each other in the proximal portion.

<3> A catheter described in <2> above, wherein the coil body is heat-treated before the distal portion of the coil body is electro-polished, so that the residual stress in the coil body is removed.

<4> A catheter described in <2> or <3> above, wherein the outer periphery of the front side of the coil body in the direction of insertion into the human body, which at least includes the tip portion of the distal portion, is centerless-ground before the distal portion of the coil body is electro-polished, so that the outer diameter of the front side of the coil body in the direction of insertion into the human body becomes smaller than the outer diameter of the rear side of the coil body in the direction of insertion into the human body, which includes the proximal portion.

<5> A catheter described in any of <1> through <4> above, wherein the inner diameter of the tip portion in the distal portion of the coil body is smaller than the inner diameter of any portion of the coil body other than the tip portion.

<6> A catheter described in <5> above, wherein a part of the distal portion of the coil body, which at least includes the tip portion, has an inner diameter and an outer diameter that both gradually decrease toward the tip.

<7> A catheter described in <5> or <6> above, wherein the minimum inner diameter of the distal portion of the coil body is larger than the outer diameter of a guide wire to be inserted axially movably into the catheter body comprising the coil body, by a dimension corresponding to 5 to 20% of the outer diameter of the guide wire.

<8> A catheter described in any of <1> through <7> above, wherein the distance between each pair of the metal wires running adjacent to each other in the distal portion of the coil body corresponds to 8 to 15% of the pitch in the distal portion.

<9> A catheter described in any of <1> through <8> above, wherein the maximum outer diameter in the distal portion of the coil body is in a range of 0.85 to 0.90 mm.

<10> A catheter including a catheter body of a specified length to be inserted into the human body; wherein the catheter body comprises a coil body formed by winding or stranding metal wires; wherein the inner diameter and outer diameter of an end at the front side of the coil body in the direction of insertion into the human body become gradually smaller toward the front; and wherein the minimum inner diameter of the end at the front side of the coil body is larger than the outer diameter of a guide wire to be inserted axially movably into the catheter body comprising the coil body, by a dimension corresponding to 5 to 20% of the outer diameter of the guide wire.

<11> A catheter described in <10> above, wherein the maximum outer diameter of the end at the front side of the coil body is in a range of 0.85 to 0.90 mm.

<12> A catheter described in any of <1> through <11> above, wherein the coil body comprises a stranded coil made by stranding a plurality of the metal wires.

<13> A method of producing a catheter including a catheter body of a specified length to be inserted into the human body, comprising: (a) a step in which metal wires are wound or stranded at a constant pitch to create a coil body having a distal portion and a proximal portion, and then the obtained coil body is used to produce the catheter body; and (b) a step in which the surface of the metal wires in the distal portion of the coil body is electro-polished to create a gap between each pair of adjacent metal wires in the distal portion, so that the distance between each pair of the metal wires running adjacent to each other in the distal portion becomes larger than the distance between each pair of the metal wires running adjacent to each other in the proximal portion.

<14> A method of producing a catheter described in <13> above, further comprising a step in which the coil body is heat-treated before the distal portion of the coil body is electro-polished, so that the residual stress in the coil body is removed.

<15> A method of producing a catheter described in <13> or <14> above, further comprising a step in which the outer periphery of the front side of the coil body in the direction of insertion into the human body, which at least includes the tip portion of the distal portion, is centerless-ground before the distal portion of the coil body is electro-polished, so that the outer diameter of the front side of the coil body becomes smaller than the outer diameter of the rear side of the coil body in the direction of insertion into the human body, which includes the proximal portion.

<16> A method of producing a catheter described in any of <13> through <15> above, further comprising a step in which the tip portion of the distal portion is swaged before the distal portion of the coil body is electro-polished, so that the inner diameter of the tip portion becomes smaller than the inner diameter at any portion of the distal portion other than the tip portion.

<17> A method of producing a catheter described in any of <13> through <16> above, wherein the coil body is made by winding or stranding a plurality of the metal wires at a constant pitch.

<18> A method of producing a catheter described in any of <13> through <17> above, wherein the distance between each pair of adjacent metal wires in the distal portion of the coil body corresponds to 8 to 15% of the pitch in the distal portion.

<19> A method of producing a catheter described in any of <13> through <18> above, wherein the maximum outer diameter in the distal portion of the coil body is in a range of 0.85 to 0.90 mm.

<20> A method of producing a catheter described in any of <13> through <19> above, wherein the minimum inner diameter in the distal portion of the coil body is larger than the outer diameter of a guide wire to be inserted axially movably into the catheter body comprising the coil body, by a dimension corresponding to 5 to 20% of the outer diameter of the guide wire.

In this specification, the pitch of the coil body (stranding length) refers to the length, measured in parallel with the axial direction, of a single wire rotating once around the axis (core wire) in a manner forming a perfect helix.

In essence, a catheter according to at least one embodiment of the present invention has substantially or nearly the same pitches in the distal portion and proximal portion of the coil body, while the distance between each pair of metal wires in the distal portion is larger than the distance between each pair of metal wires in the proximal portion, so that higher flexibility can be ensured in the distal portion than in the proximal portion without reducing the rigidity in the proximal portion.

For the above reason, such catheter can fully exhibit sufficient flexibility to move along meandering blood vessels, as well as good torque transmissibility, even when the coil body is made of relatively thick metal wires so as to provide an outer diameter needed to dilate an occluded area in the blood vessel to a size at which a large balloon catheter can be inserted.

Therefore, use of a catheter according to at least one embodiment of the present invention allows for simple, quick and safe operation of a procedure in which an occluded area in a blood vessel is dilated to a size at which a large balloon catheter can be inserted using the coil body alone, without using a small balloon catheter, in a manner not reducing the operation performance of the coil body during the aforementioned procedure. As a result, the burdens on the operator performing a procedure to dilate an occluded area in a blood vessel, and also on the patient receiving the procedure, can be reduced in a very effective manner.

With an another catheter according to at least one embodiment of the present invention, the inner diameter and outer diameter at the front-side end of the coil body become gradually smaller toward the front, which further enhances the flexibility at the front-side end of the coil body. In addition, the minimum inner diameter at the front-side end of the coil body is larger than the outer diameter of the guide wire by a dimension corresponding to 5 to 20% of the outer diameter of the guide wire. Therefore, the difference between the minimum inner diameter at the front-side end of the coil body and the outer diameter of the guide wire to be inserted into the coil body can be effectively reduced, even when the outer diameter of the coil body is set to a size that allows for dilation of an occluded area in a blood vessel to a size at which a large balloon catheter can be inserted. As a result, the coil body can be guided by the guide wire in a favorable, stable manner.

For the above reason, a catheter according to at least one embodiment of the present invention allows for operation of a procedure in which an occluded area in a blood vessel is expanded to a size at which a large balloon catheter can be inserted using the coil body alone, in a very simple, quick manner without reducing in any way the operation performance of the coil body in the blood vessel.

Furthermore, a method of producing a catheter according to at least one embodiment of the present invention allows for production in a favorable manner of a coil body as a catheter body that has substantially or nearly the same pitches at its distal portion and proximal portion, while the distance between each pair of metal wires in the distal portion is larger than the distance between each pair of metal wires in the proximal portion.

Therefore, such method of producing a catheter according to at least one embodiment of the present invention allows for production in a very favorable manner of a catheter that can be used in a smooth, efficient and safe operation of a procedure in which an occluded area in a blood vessel is dilated to a size at which a large balloon catheter can be inserted.

Also, such method of producing a catheter according to at least one embodiment of the present invention provides electro-polishing of the metal wires in the distal portion of the coil body, so that the distance between each pair of adjacent metal wires becomes larger in the distal portion than in the proximal portion. Therefore, torque transmissibility of the coil body can be favorably enhanced compared with when, for example, a coil body is formed by using thick metal wires to form the proximal portion and using thinner metal wires to form the distal portion at a pitch substantially or nearly the same as the pitch in the proximal portion, and then bonding the metal wires in the proximal portion with those in the distal portion.

For this reason, such method of producing a catheter according to at least one embodiment of the present invention allows for production in a more favorable manner of a catheter that can be used to operate in a more favorable manner the procedure in which an occluded area in a blood vessel is dilated to a size at which a large balloon catheter can be inserted.

To describe the present invention in a more specific manner, the structures of catheters and their production methods according to at least one embodiment of the present invention are explained in details by referring to the drawings.

Figure 2:
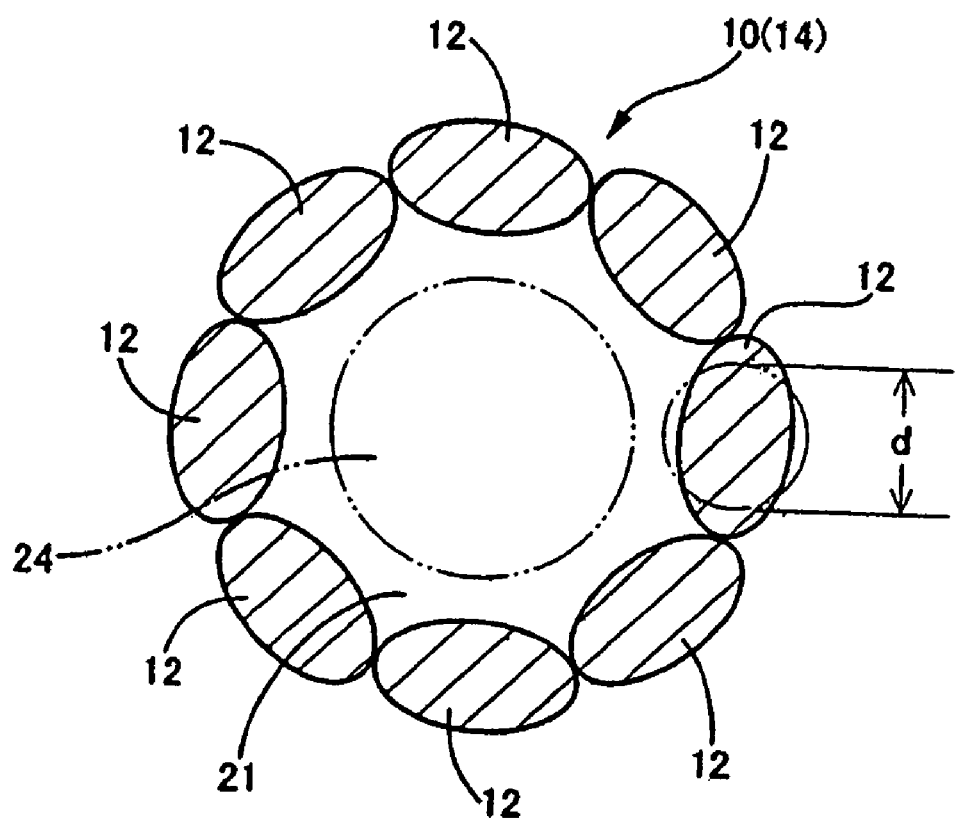
FIG. 2 is an explanatory diagram showing an enlarged end view, taken along II-II of FIG. 1.

FIGS. 1 and 2 show one embodiment of catheter having a structure according to at least one embodiment of the present invention. The figures show a front view and lateral cross-section view, respectively, of a catheter that can be inserted into a cardiovascular vessel in which an occluded area is formed, in order to dilate the occluded area in the blood vessel. As shown in these figures, the catheter in this embodiment comprises a coil body (10) as the catheter body.

Figure 5:
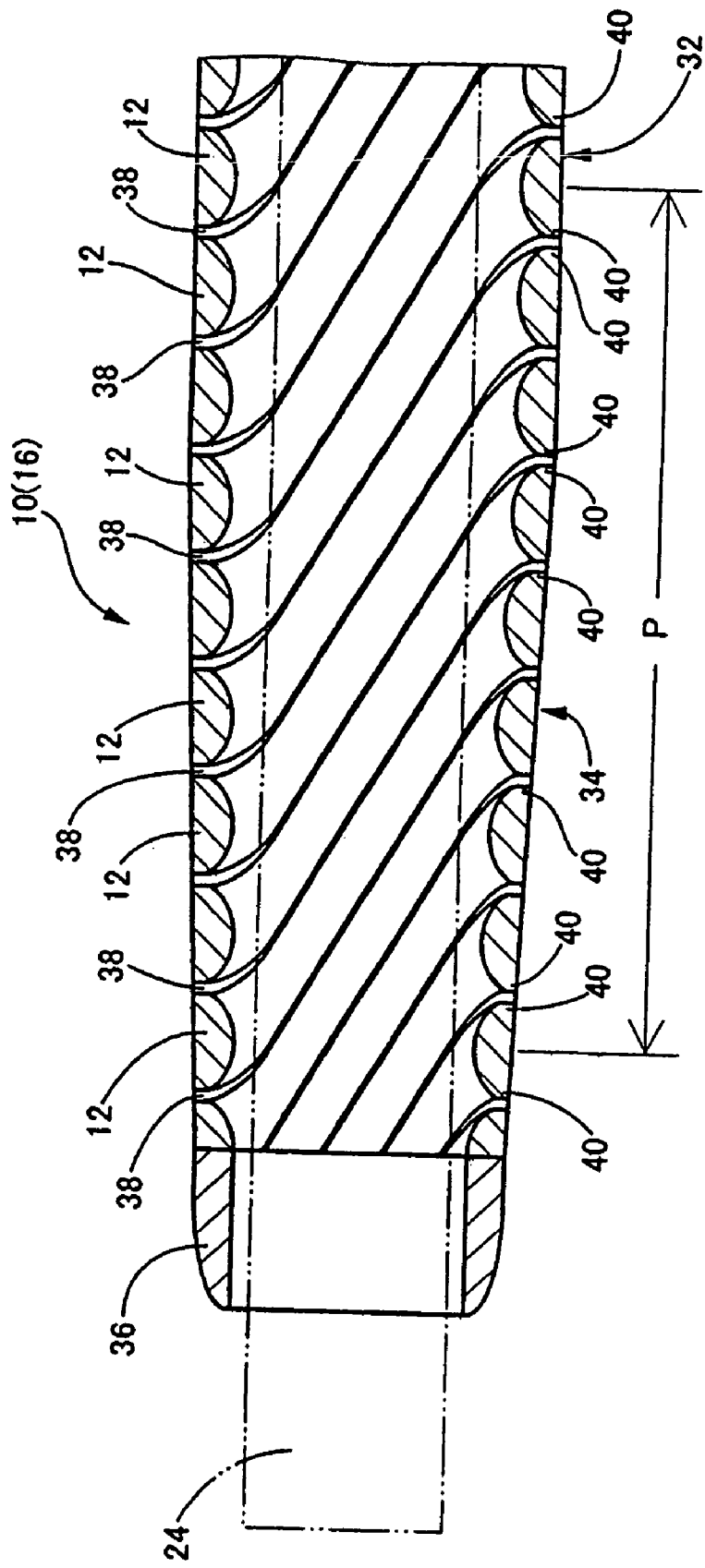
FIG. 5 is an explanatory diagram showing a partially enlarged view, taken along V-V of FIG. 3.

To be specific, this coil body (10) comprises a stranded coil made by closely stranding multiple pieces (eight in this embodiment) of a long, thin wire (12) at a constant pitch of approx. 1.78 mm (dimension indicated by P in FIG. 5). Each wire (12) comprising the coil body (10) is made of a stainless steel wire material having a circular lateral cross section (shape indicated by alternate long and two short dashes line in FIG. 2) and a relatively large diameter of approx. 0.18 mm (dimension indicated by d in FIG. 2). The coil body (10) also has a long, thin cylindrical shape of a maximum outer diameter (such as approx. 1.0 mm) and length (such as 1,350 mm) at which the coil body can be inserted into human blood vessels extending from the thighs or wrists to the heart, over the entire lengths of the blood vessels. In FIG. 2, the wires (12) are shown to have an oval lateral cross-section shape. It should be understood that this coil, stranded in the step of forming the coil body (10), is cut along a plane vertical to the axial direction, and that the oval lateral cross-section shape results from deformation of the coil due to the large load applied when the wires were stranded.

This coil body (10) having the aforementioned structure provides both sufficient flexibility and appropriate rigidity. This flexibility and rigidity does not change at any part along the longitudinal direction due to an increase or decrease of pitch P. This way, the coil body (10) can be smoothly inserted into meandering blood vessels.

The material for wires (12) is not at all limited to stainless steel used in this example. The wires (12) can be made of any flexible metal material that has been traditionally used to produce catheter components. For example, Ni—Ti alloy or other super-elastic alloy can be used on its own or in combination with stainless steel.

In addition, the number of wires (12) can be determined freely as deemed appropriate in accordance with, for example, the balance of flexibility and rigidity expected of the coil body (10). In other words, it is acceptable to form a coil body (10) by winding one wire (12). To achieve good torque transmissibility based on appropriate rigidity, while maintaining sufficient flexibility, a coil body (10) may be formed preferably by stranding multiple wires (12), or more preferably by stranding eight to 12 wires (12).

Furthermore, diameter d of the wire (12) is not at all limited. Desirably, the diameter may be in a range of 0.16 to 0.20 mm. If diameter d of the wire (12) is less than 0.16 mm, the wire (12) becomes too thin and the rigidity of the coil body (10) may become insufficient. If diameter d of the wire (12) exceeds 0.20 mm, the wire (12) becomes too thick and the coil body (10) becomes too rigid, which makes it difficult to smoothly insert the coil body into meandering blood vessels.

Furthermore, the pitch P of the coil body (10) is not at all limited, either, and it can be changed freely as deemed appropriate in accordance with diameter d of the coil (12), etc., as long as the pitch is kept identical over the entire length of the coil body (10). For example, if diameter d of the wire (12) is 0.18 mm, then pitch P can be set in a range of 1.70 to 1.90 mm. This is because setting pitch P of the coil body (10) to a dimension greater than 1.90 mm may reduce the rigidity of the coil body (10). If pitch P of the coil body (10) is to be made smaller than 1.70 mm, the wires (12) must be stranded with a very large force. Such operation costs high, and production of a coil body in this manner is practically difficult.

In this embodiment, the coil body (10) comprises: a proximal portion (14) covering the end at the rear side of the coil body with respect to the direction of insertion into the blood vessel; a distal portion (16) covering the end at the front side of the coil body with respect to the direction of insertion; and an intermediate portion (18) covering the section between the proximal portion (14) and distal portion (16). To facilitate understanding of the structure of the coil body (10) and that of the entire catheter, the distal portion (16) side of the coil body (10) is hereinafter referred to as the "front side," while the proximal portion (14) side is referred to as the "rear side." A portion including both the intermediate portion (18) and the proximal portion (14), which is not surface-treated by, for example, centerless-grinding or swaging, may be referred to as the "proximal portion."

Of the three portions (14, 16, 18) comprising the coil body (10), the entire proximal portion (14) has a cylindrical shape with an outer diameter of approx. 1.0 mm and an inner diameter of approx 0.64 mm. Furthermore, the rear end of the proximal portion (14) is coupled with a connector (20). An inner bore of this proximal portion (14) connects to a through hole in the connector (20), and then opens to outside via the through hole. In the proximal portion (14), a section that is not inserted into a blood vessel has a cover tube (22) inserted over the non-inserted section of the proximal portion.

In this embodiment, a guide wire (24) (indicated by alternate long and two short dashes line in FIG. 2) generally having a diameter of approx. 0.36 mm is axially movably inserted into the inner bore (21) of the coil body (10), via the connector (20). If blood leaks through the gaps between the wires (12) composing the coil body (10) while the coil body (10) is inserted into a blood vessel, the cover tube (22) prevents the hands of an operator from contacting the blood.

Figure 3:
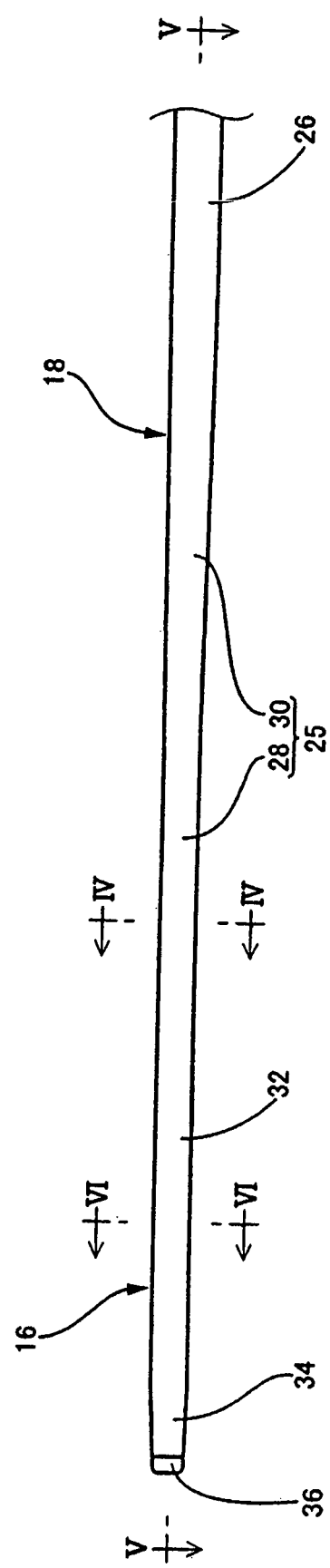
FIG. 3 is an explanatory diagram showing a partially enlarged view of FIG. 1.

As shown in FIGS. 1 and 3, most of the intermediate portion (18) of the coil body (10), except for a front-side portion (25), comprises an intermediate large-diameter cylinder portion (26) having the same outer diameter and inner diameter as the proximal portion (14). Furthermore, at the front-side portion (25) of the intermediate portion (18), the front end comprises an intermediate small-diameter cylinder portion (28) having the same inner diameter as the intermediate large-diameter cylinder portion (26) and an outer diameter smaller than that of the intermediate large-diameter cylinder portion (26). Moreover, this intermediate portion (18) between the intermediate large-diameter cylinder portion (26) and the intermediate small-diameter cylinder portion (28) comprises an intermediate tapered portion (30) having the same inner diameter as the intermediate large-diameter cylinder portion (26) and the intermediate small-diameter cylinder portion (28), but whose outer diameter gradually decreases toward the front.

In other words, the inner diameters of the intermediate large-diameter cylinder portion (26), intermediate small-diameter cylinder portion (28) and intermediate tapered portion (30) are the same as the inner diameter of the proximal portion (14), or approx. 0.64 mm. Also, the outer diameter of the intermediate large-diameter cylinder portion (26) is the same with the proximal portion (14), or approx. 1.0 mm. And, the outer diameter of the intermediate tapered portion (30) decreases from approx. 1.0 mm corresponding to the outer diameter of the proximal portion (14), to approx. 0.88 mm. The outer diameter of the small-diameter cylinder portion (28) is sufficient to insert a large balloon catheter used in a procedure to expand an occluded area in a blood vessel. The length of the intermediate tapered portion (30) is approx. 50.0 mm. The length of the intermediate small-diameter cylinder portion (28) is approx. 30.0 mm.

Figure 4:
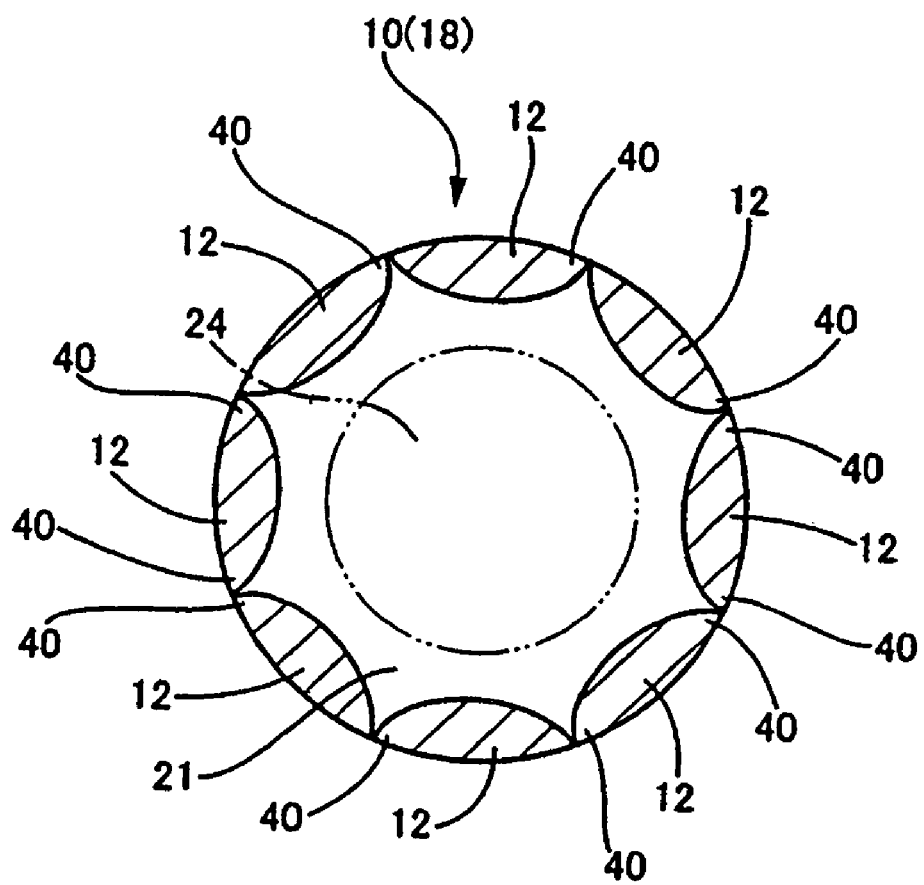
FIG. 4 is an explanatory diagram showing an enlarged end view, taken along IV-IV of FIG. 3.

As shown in FIG. 4, the outer periphery of the front-side portion (25) of the intermediate portion (18) is shaved, ground or otherwise removed to lessen the outer periphery over each wire (12). The outer diameters of the intermediate small-diameter cylinder portion (28) and intermediate tapered portion (30) comprising the front-side portion (25) are smaller than the outer diameter of the unprocessed intermediate large-diameter cylinder portion (26) or proximal portion (14). This way, the lateral cross-section shape of each wire (12) becomes a flat shape expanding in the circumferential direction of the intermediate portion (18), and these intermediate small-diameter cylinder portion (28) and intermediate tapered portion (30) have thin walls as a result. These thin walls of the intermediate small-diameter cylinder portion (28) and intermediate tapered portion (30) can be easily achieved by, for example, grinding the front-side portion (25) of the intermediate portion (18) comprising the intermediate small-diameter cylinder portion (28) and intermediate tapered portion (30) by means of centerless grinding using a centerless grinder.

On the other hand, as shown in FIGS. 3 and 5, the rear side of the distal portion (16) comprises a tip cylinder portion (32) that continues to the intermediate small-diameter cylinder portion (28) of the intermediate portion (18). The front side comprises a tip tapered portion (34) whose outer diameter and inner diameter both decrease gradually toward the tip. Specifically, the outer diameter of the tip cylinder portion (32) of the distal portion (16) is approx. 0.88 mm, while its inner diameter is approx. 0.64 mm. Also, the outer diameter of the tip tapered portion (34) decreases from approx. 0.88 mm to approx. 0.70 mm. Furthermore, its inner diameter decreases from approx. 0.64 mm to approx. 0.40 mm, which is a dimension slightly larger than the general diameters (approx. 0.36 mm) of guide wires (24) inserted into cardiovascular vessels. The length of the tip cylinder portion (32) is approx. 45.0 mm. The length of the tip tapered portion (34) is approx. 5.0 mm, including the length of a tip end (36) explained later.

Figure 6:
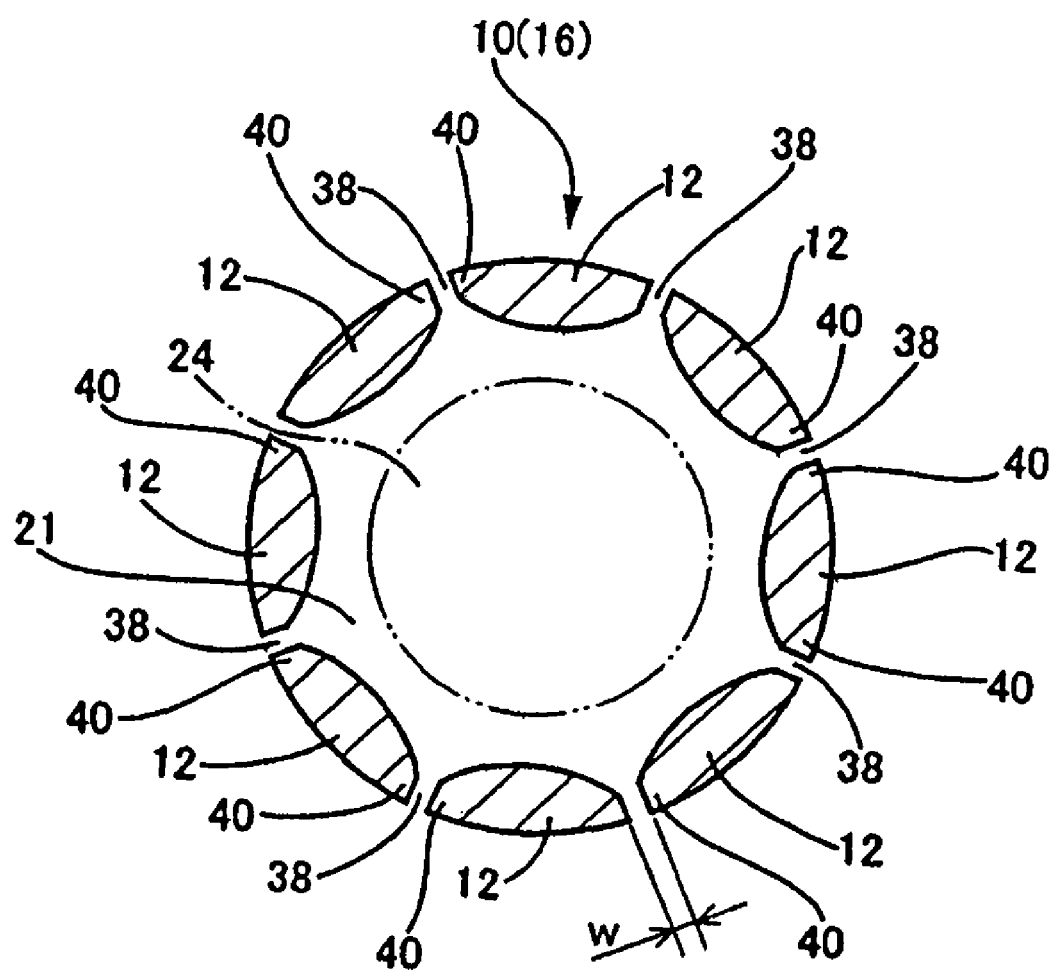
FIG. 6 is an explanatory diagram showing an enlarged end view, taken along VI-VI of FIG. 3.

In FIGS. 5 and 6, the wires (12) in the distal portion (16) have a flat lateral cross-section shape expanding in the circumferential direction of the distal portion (16), wherein the shape is formed by means of shaving, grinding or otherwise lessening the outer periphery over the distal portion (16), in the same manner as the outer periphery is removed over the intermediate small-diameter cylinder portion (28) and intermediate tapered portion (30) of the intermediate portion (18), in order to achieve thin walls over the entire distal portion (16). These thin walls of the distal portion (16) can also be achieved by means of centerless grinding using a centerless grinder. The tip tapered portion (34) at which both the outer diameter and inner diameter gradually decrease can be easily formed by, for example, swaging the tip portion of the distal portion (16).

Also, the tip surface of the tip tapered portion (34) in the distal portion (16) has a tip end (36) affixed to it. This tip end (36) is formed by a cylinder body, which is in turn made of gold, platinum, platinum rhodium or other radio-opaque material. The outer periphery of the tip cylinder portion on the opposite side of the distal portion (16) at which the tip end is affixed, has a concave curved surface whose diameter gradually decreases toward the tip. This way, the thickness of the tip cylinder portion at the tip end (36) decreases gradually toward the tip, thus causing the tip end (36) to have a tapered shape. The maximum outer diameter and inner diameter of this tip end (36) are the same as the outer diameter and minimum inner diameter of the tip tapered portion (34) of the distal portion (16), respectively.

Here, among the multiple wires (12) comprising the distal portion (16), each pair of wires running adjacent to each other has a gap (38) formed between them in the longitudinal direction of the coil body (10). As shown in FIGS. 4 and 6, this gap (38) is formed between edges (40) of adjacent wires (12), as the edges (40) on both sides of each wire (12) in the width direction have been partially removed over a specified width in the distal portion (16) where the lateral cross section was made into a flat shape expanding in the circumferential direction of the distal portion (16) by means of the aforementioned centerless grinding or other thin-wall production method.

This way, as shown in FIGS. 2, 4 and 6, the distance between each pair of adjacent wires (12) in the distal portion (16) becomes larger than the distance between each pair of adjacent wires (12) in the proximal portion (14) or intermediate portion (18), by a dimension corresponding to width w of the gap (38). This gap (38) between each pair of adjacent wires (12) in the distal portion (16) can be formed easily by, for example, electro-polishing the distal portion (16).

As explained above, the outer diameter of the tip cylinder portion (32) in the distal portion (16) of the coil body (10) is approx. 0.88 mm in this embodiment. Therefore, the maximum outer diameter of the distal portion (16) is larger than the outer diameter before inflation of a large balloon catheter used generally in a procedure to expand an occluded area in a blood vessel. This way, the coil body (10) can dilate, via its distal portion (16), an occluded area in a blood vessel to a sufficient size at which a large balloon catheter can be inserted.

The maximum outer diameter of this distal portion (16) is not at all limited, but it may desirably be in a range of approx. 0.85 to 0.90 mm. If the maximum outer diameter of the distal portion (16) is smaller than 0.85 mm, it becomes difficult to use the distal portion (16) to expand an occluded area in a blood vessel to a sufficient size at which a non-inflated large balloon catheter can be inserted. If the maximum outer diameter of the distal portion (16) exceeds 0.90 mm, on the other hand, the distal portion (16) becomes too rigid.

Also, the front-side end of the coil body (11), comprising the front-side portion (25) of the intermediate portion (18) as well as the distal portion (16), has thinner walls compared with other portions and a tapered shape of gradually decreasing diameter. This way, sufficient flexibility can be ensured at the front-side end even when the coil body (10) is made of wires (12) having a relatively large diameter. In addition, a gap (38) is formed between each pair of adjacent wires (12) in the distal portion (16), with pitch P maintained at the same dimension with the proximal portion (14) and intermediate portion (18). Also, the distance between these wires (12) is larger than the distance between each pair of adjacent wires in the proximal portion (14) or intermediate portion (18), so that flexibility in the distal portion (16) is enhanced further.

Width w of the gap (38) formed between each pair of adjacent wires (12) in the distal portion (16), or distance between these wires (12), is not at all limited. Ideally, however, the sum of the gaps or the total distance between the respective wires per pitch P may correspond to 8 to 15% of pitch P in the distal portion (16). If the aforementioned distance is less than 8% of pitch P in the distal portion (16), desired flexibility cannot be achieved sufficiently in the distal portion (16). If the aforementioned distance exceeds 15% of pitch P in the distal portion (16), the distal portion (16) becomes too flexible and the strength and torque transmissibility may drop. More ideally, this distance between each pair of adjacent wires (12) in the distal portion (16) may correspond to 10% of pitch P in the distal portion (16).

In the tip tapered portion (34) of the distal portion (16) of this coil body (10), the minimum inner diameter is larger than the aforementioned general diameter (approx. 0.36 mm) of the guide wire (24) inserted into the coil body (10), by approx. 0.04 mm by dimension, or approx. 11.1% by ratio. This way, an appropriate gap can be created between the inner periphery of the coil body (10) and the outer periphery of the guide wire (24) in such a way that the guide wire (24) will not cause a significant run-out or other problem in the distal portion (16) of the coil body (10) while the guide wire (24) is inserted into the coil body (10). For this reason, the coil body (10) can be guided by the guide wire (24) in a stable, appropriate manner.

The minimum inner diameter in the distal portion (16) of this coil body (10) is not at all limited, either, but it may desirably be larger than the outer diameter of the guide wire (24) by a dimension corresponding to 5 to 20% of the outer diameter. If the minimum inner diameter in the distal portion (16) is smaller than the minimum value of the aforementioned range, the gap between the inner periphery of the distal portion (16) and the outer periphery of the guide wire (24)

becomes too small, which prevents smooth axial-direction movement of the guide wire (24) in the distal portion (16). If the minimum inner diameter in the distal portion (16) is larger than the maximum value of the aforementioned range, the gap between the inner periphery of the distal portion (16) and the outer periphery of the guide wire (24) becomes too large, which makes the guiding of the coil body (10) by the guide wire (24) unstable.

In the above, the boundary between the tip cylinder portion (32) of the distal portion (16) and the intermediate small-diameter cylinder portion (28) of the intermediate portion (18) is a boundary where the gap between wires is changed. That is, the distal portion (16) is, for example, electro-polished whereas the intermediate portion (18) is not electro-polished, i.e., the tip cylinder portion (32) is electro-polished whereas the intermediate small-diameter cylinder portion (28) is not electro-polished. Thus, before the electro-polishing, for example, there may be no material difference between the tip cylinder portion (32) of the distal portion (16) and the intermediate small-diameter cylinder portion (28) of the intermediate portion (18). The boundary may not be visibly recognizable but can be recognized using a magnification camera.

The boundary between the proximal portion (14) and the intermediate portion (18) may not be clear. The configuration of the intermediate large-diameter cylinder portion (26) of the intermediate portion (18) and the configuration of the proximal portion (14) may substantially be the same. That is, both portions are not surface-treated such as centerless-grinding. The portions which are not surface-treated may be referred to generally as the "proximal portion" which includes the intermediate portion (18) and the proximal portion (14).

For example, the length of each portion may be as follows:

| Section | Sub-section | Range [mm] | Example [mm] |
|---|---|---|---|
| Entire distal portion 16 | | 5.0-250.0*[1] | 50.0 |
| Distal portion 16 | Tip portion 36 | 0.5-1.5 | 1.0 |
| | Tip-tapered portion 34 | 0.5-10.0*[2] | 4.0 |
| | Tip cylindrical portion 32 | 0-249.0*[3] | 45.0 |
| Intermediate portion 18 | Intermediate small-cylindrical portion 28 | 0-250.0*[4] | 30.0 |
| | Intermediate tapered portion 30 | 10.0-200.0*[5] | 50.0 |
| | Intermediate large-cylindrical portion 26 | 700.0-900.0*[6] | |
| Proximal portion 14 | | 300-500*[7] | |
| Total of distal, intermediate, and proximal portions | | 1,320-1,400*[8] | 1,350.0 |

*[1] This range is set for inserting the portion into a cardiovascular vessel.
*[2] The length of the tapered portion is preferably short. However, if it is too short, the angle of the taper with respect to the axial direction is too large, and in this case, the tapered angle of an inner wall of the portion also becomes large, which may interfere with movement of a guide wire.
*[3],*[4] The tip cylindrical portion 32 and the intermediate small-cylindrical portion 28 can be eliminated if the diameter of the proximal portion 14 is not large (e.g., 0.90 mm). If the diameter of the proximal portion 14 is large, these plateau portions may be necessary in order to practically gradually reduce the diameter of the catheter toward the tip end. If no tip cylindrical potion 32 is formed, the wires only in the tip-tapered portion 34 are spaced more than those in the other portions.
*[5] This is a general range necessary for practically gradually reduce the diameter of the catheter.
*[6],*[7] These ranges can be determined by subtracting the total lengths of the portions 36, 34, 28, and 30 from the entire length of the catheter. The lengths of the portions 36, 34, 28, and 30 are more important than the lengths of these portions.
*[8] This range is set for a catheter for a cardiovascular vessel. For other purposes such as vessels in legs, the total length may be 500 mm to 2,000 mm. In this case, the length of the intermediate large-cylindrical portion 26 and the length of the proximal portion 14 may be adjusted.

The catheter having the aforementioned structure as provided by this embodiment can be produced in the following method, among others.

Specifically, multiple pieces (eight in this case) of a long wire (12) are prepared. These wires (12) have a length sufficiently longer than the intended catheter. The prepared multiple wires (12) are then stranded at a constant pitch around a specified core wire using a method similar to one used in the production of general stranded coils. This produces a stranded rope being an intermediate product of the coil body (10).

Next, the obtained stranded rope is tentatively cut to a specified length. The tentative cutting length of the stranded rope in this step can be determined freely as deemed appropriate in accordance with, for example, the size of the processing apparatus used for heat-treating the stranded rope (heat treatment is explained later on).

Figure 7:
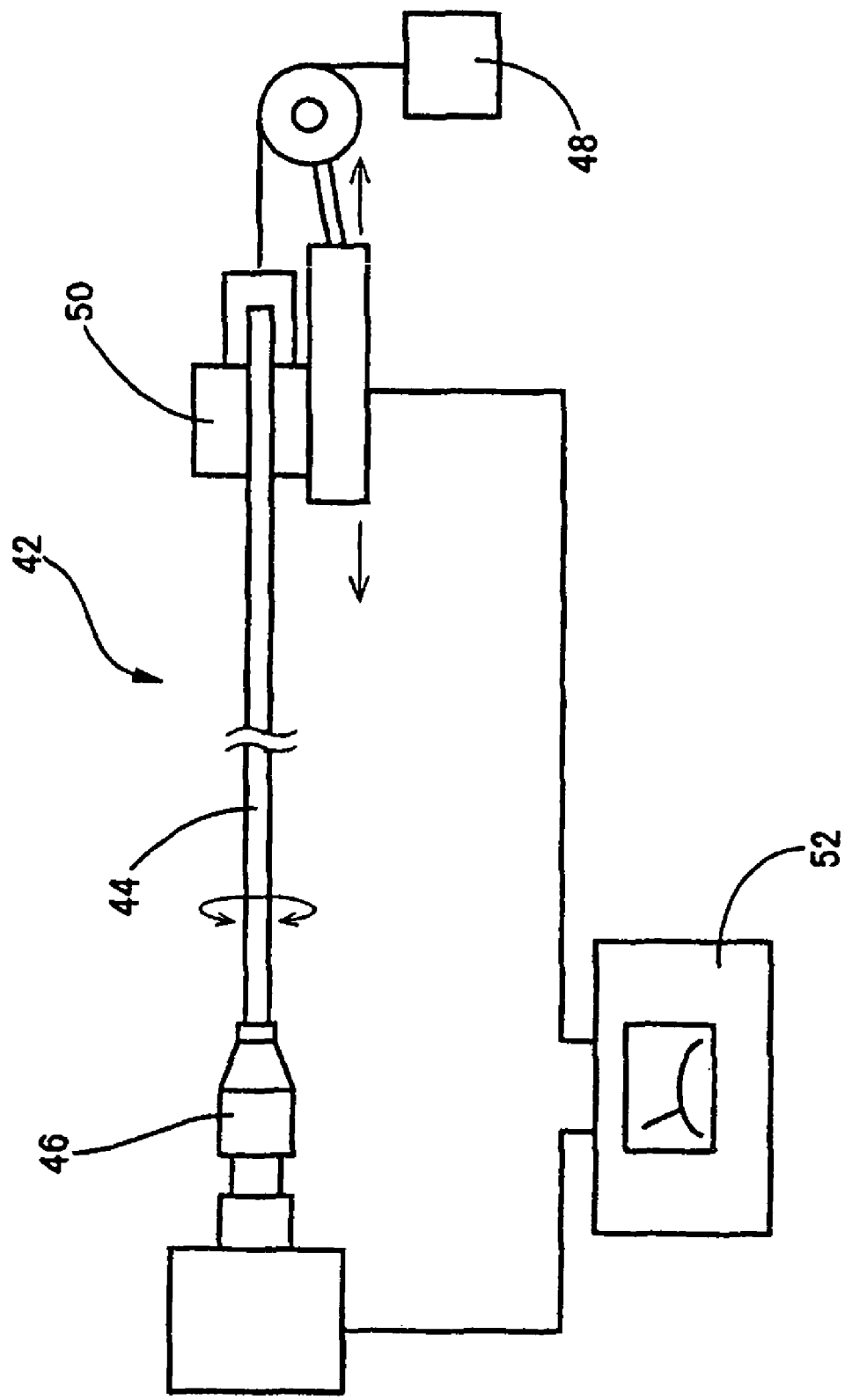
FIG. 7 is an explanatory diagram showing an example of production process of the catheter shown in FIG. 1. Specifically, the figure illustrates how the coil body of this catheter is heat-treated.

Next, a heat treatment apparatus (42) like the one shown in FIG. 7 is used to apply heat treatment to a stranded rope (44) that has been cut tentatively. Specifically in this step, one end of the stranded rope (44) is gripped by a moving chuck (46) of the heat treatment apparatus (42), while the other end of the stranded rope (44) is gripped by a slide chuck (50) from which a weight (48) is suspended. With the stranded rope (44) receiving a tensile load by the weight (48), the moving chuck (46) is turned for a specified number of revolutions each in the forward direction and reverse direction. This way, the stranded rope (44) is twisted in the forward direction and reverse direction around the axis. While the moving chuck (46) is turned, current is supplied to the moving chuck (46) and slide chuck (50) from a current generator (52) to heat the stranded rope (44) by means of resistance heating. This effectively gives heat treatment to the stranded rope (44), thus removing the residual stress generated in the wires (12) of the stranded rope (44) in the stranding step. The wires (12) are shaped through the above procedure. Of course, the heat treatment given in this step can be implemented by using an apparatus other than the heat treatment apparatus (42) shown in the example.

Next, a known centerless grinder is used to grind the outer periphery at one end of the stranded rope (44) in the longitudinal direction. Specifically in this step, one end of the stranded rope in the longitudinal direction is rotatably supported at the support of the centerless grinder. Also, two grinding rolls are positioned on both sides of the stranded rope (44) in such a way that the distance between the rolls can be adjusted and that the rolls are axially movable. Then, the stranded rope (44) is turned via rotation of these two grinding rolls, while at the same time the outer periphery of the stranded rope (44) is ground by the two grinding rolls. At this time, the two grinding rolls move in the axial direction while changing the distance in between.

Thus the wires (12) comprising the stranded rope (44) are ground in a manner forming a flat lateral cross-section shape in the circumferential direction of the stranded rope (44), as shown in FIG. 4. During grinding, the grinding amount of the stranded rope (44) changes as the distance between the two grinding rolls changes.

As a result, the outer periphery of the section at one end of the stranded rope (44) is formed into a tapered shape where the diameter gradually decreases toward the one end, and the intermediate tapered portion (30) is thus formed in this section having the aforementioned tapered outer periphery. Also on one end of this stranded rope (44), the area excluding the intermediate tapered portion (30) has an outer periphery of a cylinder shape having a smaller diameter than the other end portion. In this area having the aforementioned outer periphery of a small-diameter cylinder shape, the specified location on the side of the intermediate tapered portion (30) becomes the intermediate small-diameter cylinder portion (28), while the distal portion (16) is formed on the opposite side of the intermediate tapered portion (30). The obtained intermediate tapered portion (30), intermediate small-diameter cylinder portion (28) and distal portion (16) have thinner walls than the portions of the stranded rope (44) that have not been centerless-ground.

After centerless grinding, the core wire is pulled out of the stranded rope (44), and the resulting stranded rope (44) comprises a stranded coil, which in turn gives a coil body (10) having the distal portion (16), intermediate small-diameter cylinder portion (28) and intermediate tapered portion (30), in this order from the tip, on one end of the coil body in the longitudinal direction. Thereafter, oxide film, which was formed on the surface of the wires (12) when the stranded rope (44) was heat-treated as mentioned above, is removed by known means.

Next, platinum or other radio-opaque material is plasma-welded to the tip of the distal portion (16). This way, a radio-opaque part that will become the tip end (36) in the subsequent operation is formed at the tip of the distal portion (16).

Next, multiple dies divided from a single shape, each having a formed surface comprising a tapered cylinder surface, are used to swage the tip portion of the distal portion (16) of the stranded coil including the radio-opaque part. Specifically, the multiple dies divided from a single shape rotate around the tip portion of the distal portion (16) of the stranded coil, with the dies having different formed surfaces hitting the outer periphery of the tip, in order to form a tapered cylinder shape with gradually decreasing diameter in the tip portion of the distal portion (16) of the stranded coil. This way, the tip portion of the distal portion (16) of the stranded coil becomes the tip tapered portion (34) having a tapered inner periphery and a tapered outer periphery. At the same time, the area of the distal portion (16) other than the tip tapered portion (34) becomes the tip cylinder portion (32). Furthermore, the outer periphery of the radio-opaque part takes a cylinder shape and forms the external shape of the tip end (36).

Thereafter, a circular through hole with a diameter of approx. 0.4 mm is drilled or otherwise opened at the center of the radio-opaque part having a cylindrical outer periphery. As a result, a cylindrical tip end (36) is provided at the tip surface of the tip tapered portion (34) of the stranded coil.

Next, the distal portion (16) of the stranded coil is dipped, together with the tip end (36), into electro-polishing solution contained in a specified electrolytic bath to provide electro-polishing of the distal portion (16). In this step, a mixture of phosphoric acid and Electroglow can be used as the electro-polishing solution, for example. With the distal portion (16) of the stranded coil dipped in this electro-polishing solution, electric charges of specified current and voltage are applied to the stranded coil. This polishes the surface of the wires (12) in the distal portion (16) of the stranded coil. Of course, the electro-polishing solution is not at all limited to the one used in the example. In another embodiment, instead of the electro-polishing, the distance between wires in the distal portion can be adjusted by chemical polishing.

As commonly known, electro-polishing is a process to electrolyze the entire surface of the target material to give polishing effect to the material surface. In electro-polishing, corners and edges are primarily electrolyzed and polished. Accordingly, this step primarily polishes the edges (40) on both sides of each wire (12) in the distal portion (16), having a flat lateral cross-section shape given by the centerless grinding of the distal portion (16) as explained above. This way, a gap (38) is formed between each pair of adjacent wires (12) in the distal portion (16), as shown in FIGS. 5 and 6. The size of the gap (38) formed here can be controlled by, for example, adjusting the time during which the distal portion (16) is dipped into the electro-polishing solution. This dipping time can be adjusted as deemed appropriate in accordance with the concentration of electro-polishing solution, current and voltage of electric charges supplied to the stranded coil, and so on.

At this time, each wire (12) of the stranded coil is free from residual stress as a result of the aforementioned heat treatment step, and is already shaped. Therefore, formation of a gap (38) between each pair of adjacent wires (12) in the distal portion (16) will not change the pitch in the distal portion (16).

The process illustrated by FIGS. 1 through 6 has thus created a coil body (10) having a constant pitch over its entire length, wherein the distance between each pair of adjacent wires (12) in the distal portion (16) is larger than the distance between each pair of adjacent wires (12) in the intermediate portion (18) or proximal portion (14).

Thereafter, the obtained coil body (10) is cut to the necessary length, after which a cover tube (22) and a connector (20) are assembled to the proximity portion (14) of this coil body (10) to obtain the intended catheter.

In a procedure to dilute an occluded area in a cardiovascular vessel using a catheter like the one shown in this embodiment, the following procedure can be followed to perform the operation, for example.

Figure 8:
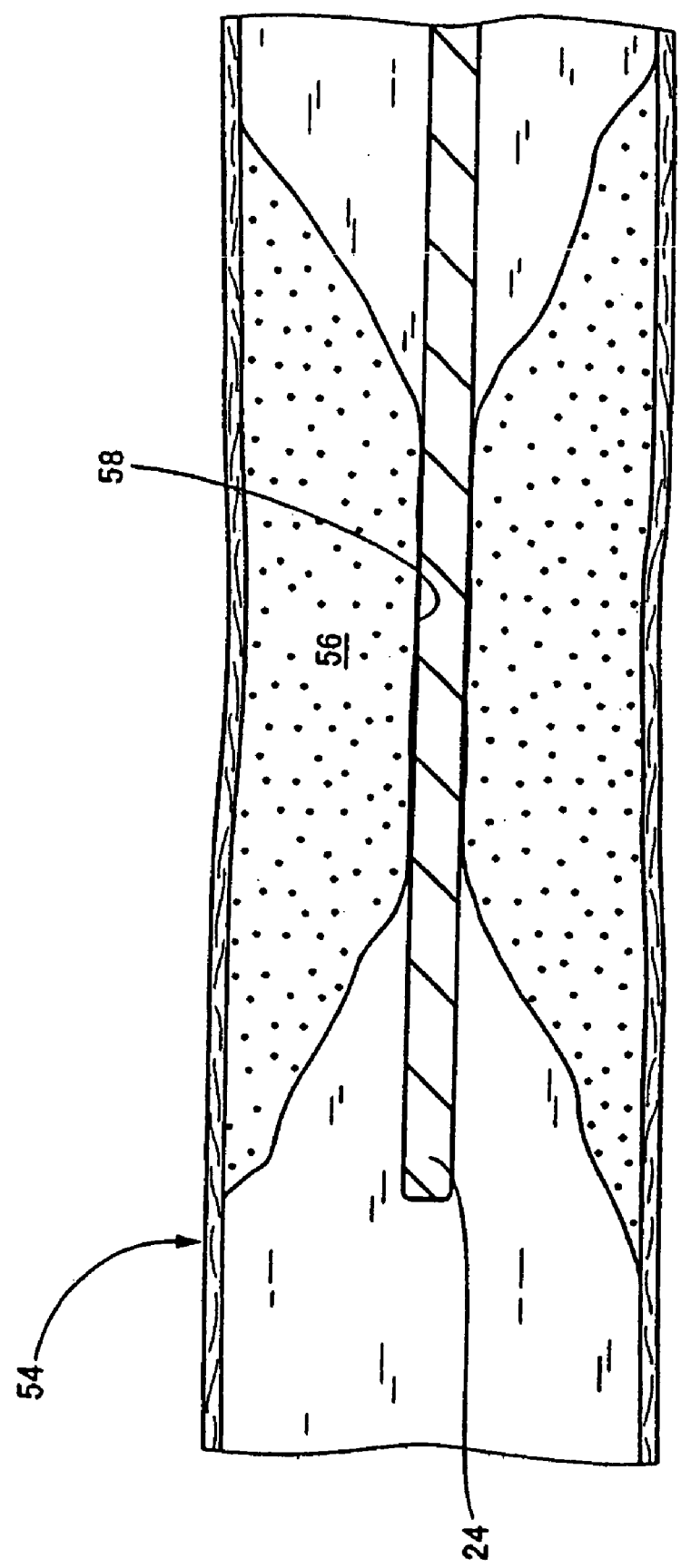
FIG. 8 is an explanatory diagram showing an example of use of the catheter shown in FIG. 1. Specifically, the figure illustrates how an insertion channel is made in an occluded area in a blood vessel using the guide wire to be inserted into this catheter.

Specifically, first the guide wire (24) is inserted into the occluded area (56) formed in the cardiovascular vessel (54), as shown in FIG. 8. This forms an insertion channel (58) in the occluded area (56). At this time, the guide wire (24) passes through a relatively soft part of the occluded area (56).

Next, the end of the guide wire (24) opposite to the one inserted into the blood vessel (54) is inserted into the coil body (10) of the catheter. This coil body (10) is then inserted into the blood vessel (54) along the guide wire (24). This operation is performed under radiography, so that the tip of the coil body (10) can be inserted reliably into the occluded area in the blood vessel (54) while checking the position of the tip end (36) made of radio-opaque material, or the tip position of the coil body (10).

At this time, the coil body (10) moves forward smoothly in the blood vessel (54) by exhibiting a good pushability characteristics and without damaging the interior walls of the blood vessel (54), due partly to the flexibility of the front-side end of the coil body (10) (the front-side portion (25) of the intermediate portion (18) and the distal portion (16)), especially the higher flexibility of the distal portion (16) of the front-side end, and partly to the appropriate rigidity exhibited by an area of the intermediate portion (18) of the coil body (10) excluding the front-side end and also by the proximal portion (14). In particular, the tip tapered portion (34) comprising the tip of the coil body (10) has a flexible structure because of the electro-polished stranded wires. Therefore, damages to the interior walls of the blood vessel (54) can be more favorably prevented when the coil body (10) is inserted into the blood vessel (54).

Furthermore, the inner diameter of the tip tapered portion (34) in the distal portion (16) of the coil body (10) is kept small, so that a gap is formed between the distal portion (16) and the guide wire (24) to allow the coil body (10) to be guided by the guide wire (24) in a stable, appropriate manner. This also ensures smooth, stable movement of the coil body (10) in the blood vessel (54).

Figure 9:
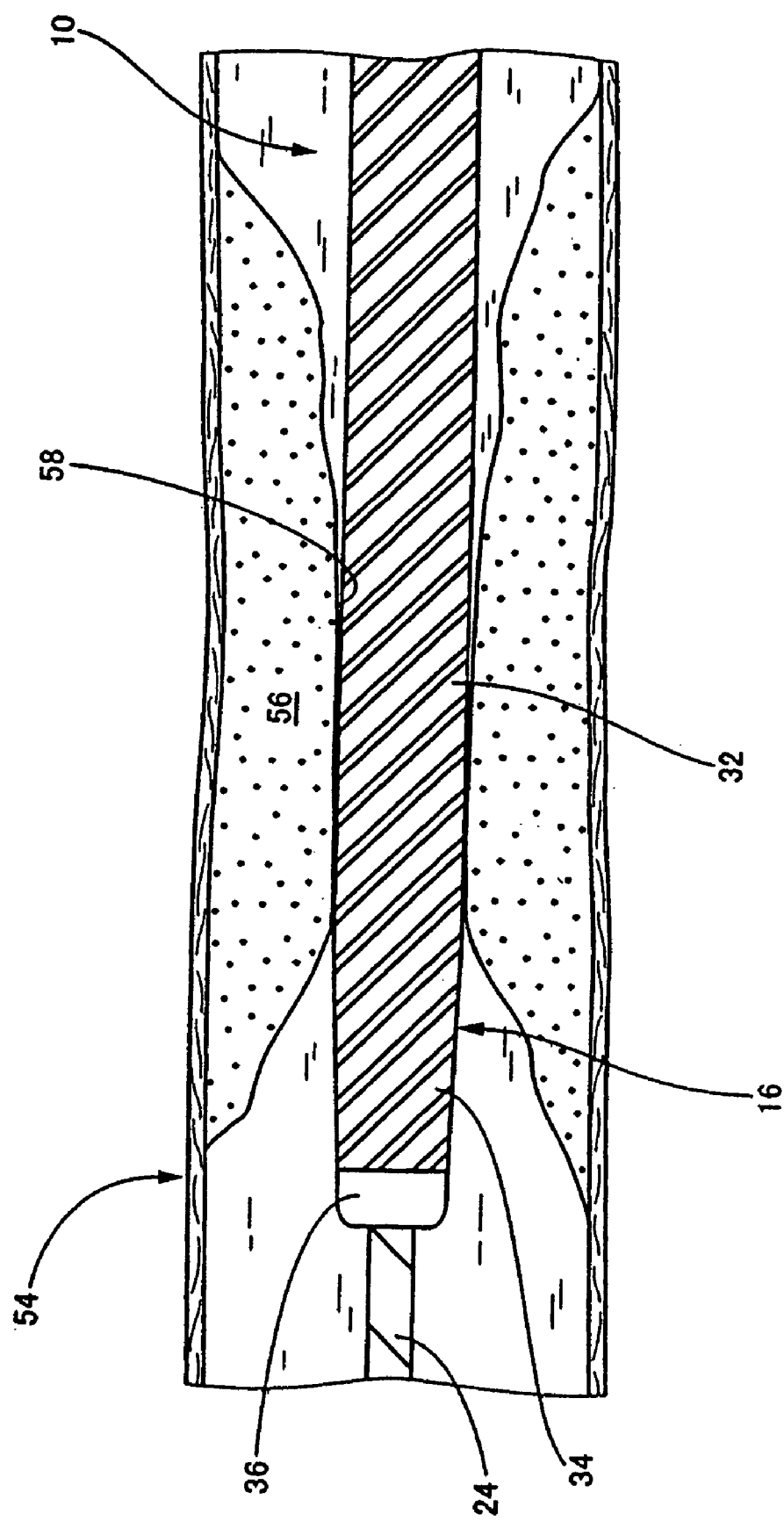
FIG. 9 is an explanatory diagram showing another example of use of the catheter shown in FIG. 1. Specifically, the figure illustrates how an occluded area in a blood vessel is enlarged by guiding the coil body of this catheter using the guide wire.

Once the tip end (36) at the tip of the coil body (10) reaches the occluded area (56) in the blood vessel (54), the proximal portion (14) of the coil body (10) is turned in order to turn the entire coil body (10), while at the same time the tip of the coil body (10) is pushed into the insertion channel (58) formed in the occluded area (56). This way, the tip end (36) and the distal portion (16) of the coil body (10) are inserted into the occluded area (56) while dilating the insertion channel (58), as shown in FIG. 9. As a result, the occluded area (56) is dilated to a size equivalent to the outer diameter of the tip cylinder portion (32) in the distal portion (16), or a size sufficient for inserting a relatively large balloon catheter.

Because the tip end (36) has a tapered shape and the tip tapered portion (34) in the distal portion (16) of the coil body (10) is also formed into a tapered shape with gradually decreasing diameter toward the tip, these tip end (36) and distal portion (16) of the coil body (10) can easily and reliably dilate the narrow insertion channel (58) as they are pushed into the channel.

Also, pitch P in the distal portion (16) of the coil body (10) is the same as pitch P in the proximal portion (14) or intermediate portion (18). Therefore, the torque applied to turn the proximal portion (14) is fully and reliably transmitted to the distal portion (14) via the intermediate portion (18) by generating minimum loss. This way, the tip end (36) and distal portion (16) can be inserted into the narrow insertion channel (58) more smoothly.

Thereafter, the coil wire (10) is pulled out of the blood vessel (54), and then a relatively large balloon catheter is inserted into the blood vessel (54) along the guide wire (24) to further expand the occluded area (56).

As explained above, in this embodiment a procedure to expand an occluded area (56) in a cardiovascular vessel (54) to a size at which a large balloon catheter can be inserted can be performed using the coil body (10) alone, without using a small balloon catheter, in a simple, quick and safe manner while stably maintaining the operation performance of the coil body during the aforementioned procedure.

Therefore, this embodiment reduces the burdens on the operator performing the procedure to expand the occluded area (56) in the cardiovascular vessel (54), and also on the patient receiving the procedure, in a very effective manner.

Also, the catheter used in this embodiment is designed so that the gap (38) between each pair of adjacent wires (12) in the distal portion (16) of the coil body (10) is formed via electro-polishing of the distal portion (16). Therefore, degradation in torque transmissibility as a result of formation of the gap (38) can be favorably prevented in the distal portion (16) compared with when, for example, a gap (38) is formed between wires (12) in the distal portion (16) by producing the distal portion (16) using wires (12) thinner than wires (12) comprising the intermediate portion (18) or proximal portion (14).

In addition, in this embodiment the wires (12) in the distal portion (16) have a flat lateral cross-section shape in the circumferential direction of the distal portion (16), because of the centerless grinding of the outer periphery of the distal portion (16) of the coil body (10). Thereafter, the distal portion (16) is electro-polished to primarily polish the edges (40) on both sides of each wire (12) in the distal portion (16), thus forming gaps (38) between the wires (12). This minimizes the decrease in lateral cross-section area of the wires (12) in the distal portion (16), while forming gaps (38) between the wires (12). Formation of these gaps (38) improves the flexibility of the distal portion (16), which in turn prevents or minimizes in a very effective manner the degradation in torque transmissibility resulting from a size reduction of wires (12).

As described above, preferably, the pitch is 1.70 mm to 1.90 mm when 8 wires are wounded or stranded. However, more generally, the pitch may be set at 1.1 mm to 2.3 mm. For example, the pitch are as follows:

| Ex. | Number of wires composing coil body | Diameter of core wire [mm] | Diameter of wire to be wound or stranded [mm] | Pitch [mm] |
|---|---|---|---|---|
| 1 | 8 | 0.45 | 0.12 | 1.22 |
| 2 | 8 | 0.45 | 0.12 | 1.19 |
| 3 | 8 | 0.5 | 0.12 | 1.21 |
| 4 | 8 | 0.6 | 0.15 | 1.53 |
| 5 | 8 | 0.66 | 0.18 | 1.81 |
| 6 | 8 | 0.75 | 0.2 | 2.21 |
| 7 | 10 | 0.45 | 0.12 | 1.72 |
| 8 | 12 | 0.35 | 0.075 | 1.29 |

In the above, the diameter of the core wire is equivalent to the diameter of the coil body. Based on the above table, a pitch can be estimated by calculation for other configurations. For example, in Ex. 1 above, if four wires are used instead of eight wires, the pitch would be reduced to ½ of the pitch of 1.22 mm.

In an embodiment, the diameter of a wire to be used may be 0.11 mm to 0.22 mm, but the width of the wire after being wound or stranded may be slightly different from the above due to the winding or stranding force toward a core metal wire.

In an embodiment, the gap between coils (wires) in the distal portion may be 0.015 mm to 0.038 mm, and in that case, if 8 wires are used, the sum of the gaps per pitch will be 0.12 mm to 0.30 mm (e.g., 5-20% of the pitch). On the other hands, the gap between coils (wires) in the proximal portion may be substantially or nearly zero.

In an embodiment, the diameter of a guide wire may be 0.25 mm to 0.46 mm, and the minimum outer diameter of the distal portion may be 0.6 mm to 0.8 mm.

Here, the inventors conducted several tests to confirm that the catheter presented in this embodiment provides the excellent characteristics mentioned above. These tests are explained in details below. The numerals specified below can be modified by ±20%.

<Test 1>

First, eight long stainless steel wires with a diameter of 0.18 mm were prepared. Then, these eight wires were stranded closely at a constant pitch of 1.7 mm to create a coil body that had substantially or nearly no gaps between the wires. Next, centerless grinding was performed on one end of this coil body using a known method to achieve an outer diameter of approx. 0.88 mm on this end.

Figure 10:
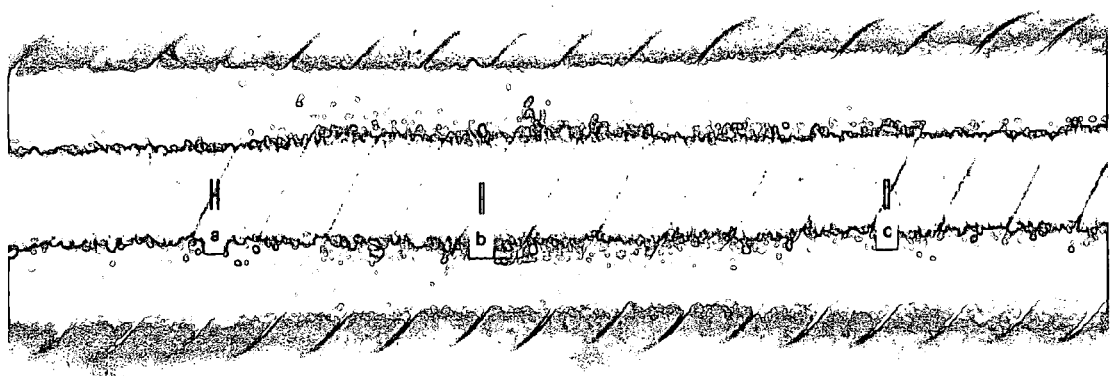
FIG. 10 is a photograph of a coil body having a centerless-ground outer periphery, which is created during a catheter production method according to at least one embodiment of the present invention.

The obtained centerless-ground end of the coil body is shown in FIG. 10. The distance between each pair of adjacent wires on this end of the coil body was measured at three randomly selected locations (locations indicated by a, b and c in FIG. 10). The measured distances were 0.009 mm at a, 0.002 mm at b, and 0.006 mm at c, which are considered to be substantially or nearly zero or which are acceptable fluctuations when zero was intended. The gap of 0.002 mm means that the wires are in fact closely in contact with each other. The measurement is obtained by viewing the area from side, and thus, even if the wires are closely in contact with each other, the measurement may not be zero. The measured pitch on this end of the coil body was 1.7 mm.

Thereafter, an electrolytic bath containing a specified amount of an electro-polishing solution consisting of phosphoric acid and Electroglow was prepared. Then, the end of the coil body as prepared above was dipped into the electro-polishing solution in this electrolytic bath to electro-polish the aforementioned end of the coil body. The electro-polishing solution was prepared by mixing phosphoric acid and Electroglow at a ratio of three to one. As for the electrolysis conditions, the electro-polishing current and time were set to 0.25 A and seven minutes, respectively, per coil body.

Figure 11:
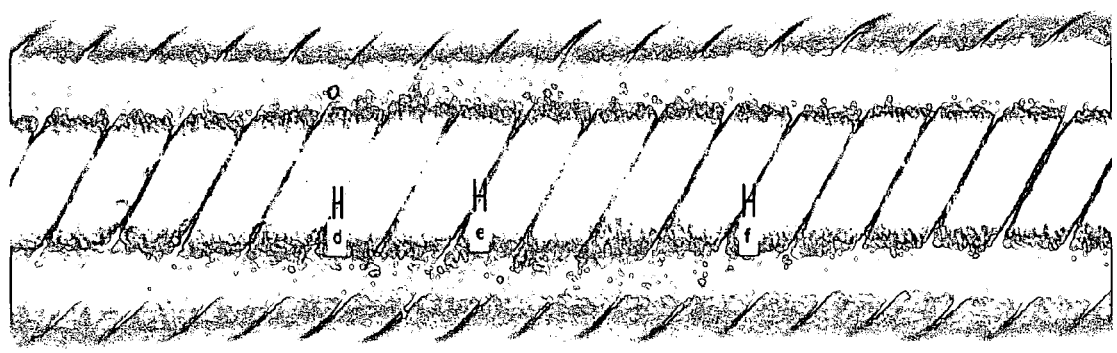
FIG. 11 is a photograph of a coil body of catheter produced in accordance with a method according to at least one embodiment of the present invention.

FIG. 11 shows the obtained coil body having an electro-polished end. The distance between each pair of adjacent wires on this electro-polished end of the coil body was measured at three randomly selected locations (locations indicated by d, e and f in FIG. 11). The measured distances were 0.023 mm at d, 0.028 mm at e, and 0.023 mm at f. The measured pitch on this end of the coil body was 1.7 mm. In the above, if each distance between two wires is 0.023 mm, the total distance between all the wires per pitch is 0.184 mm (0.023×8), which is 10.8% of the pitch (0.184/1.7). Because the electro-polishing (and prior heat-treatment) can release stress from the coil body, the gaps between the wires can uniformly be formed.

From the above results, it was found that electro-polishing the coil body would form a gap between each pair of adjacent wires and thereby increase the distance between the wires, without changing the pitch of the coil body in any way.

<Test 2>

First, 16 long stainless steel wires with a diameter of 0.18 mm and eight long stainless steel wires with a diameter of 0.15 mm were prepared. Then, the wires were divided into three groups of wires having the same diameter, and the eight wires in each group were stranded closely at a constant pitch of 1.78 mm to create two coil bodies, each made of eight wires of 0.18 mm in diameter and having substantially or nearly no gaps between the wires, and one coil body made of eight wires of 0.15 mm in diameter and having substantially or nearly no gaps between the wires. Next, centerless grinding was performed on each of the three obtained coil bodies in the same manner as in Test 1.

Then, one coil body made of eight wires with a diameter of 0.18 mm was selected from among the three centerless-ground coil bodies, and electro-polishing was performed on the centerless-ground end of this coil body under the same conditions as in Test 1. This formed a gap between each pair of adjacent wires on one end of the coil body made of eight wires with a diameter of 0.18 mm, in order to make the distance between each pair of adjacent wires on this end larger than the distance between each pair of adjacent wires on the other end that was not electro-polished.

This way, a coil body (Sample 1) made of wires with a diameter of 0.18 mm and having gaps between wires at one end with larger wire gaps on this end than on the other end, a coil body (Sample 2) made of wires with a diameter of 0.18 mm and having substantially or nearly no gaps between wires, and a coil body (Sample 3) made of wires with a diameter of 0.15 mm and having substantially or nearly no gaps between wires were produced.

Next, a torsion test was conducted on each of the obtained three coil bodies (Samples 1 to 3) to check the torque transmissibility of each coil. This torsion test was conducted by means of affixing the centerless-ground end of each coil body, and then turning the other end via a torque gauge to apply a torsional force to the entire coil body. This test was continued until at least one of the eight wires composing each coil body broke. The relationship of the number of times the coil body had been turned when the breaking occurred, and the corresponding torque load measured with the torque gauge, was checked for each coil body. The results are shown in FIG. 12.

In this test, the number of times each coil body had been turned when its wire broke (number of revolutions to breaking) and the corresponding torque load (breaking load) were as follows. The number of revolutions to breaking and breaking load of the coil body provided as Sample 1 were 44.5 times and 0.44 N-cm, respectively. The number of revolutions to breaking and breaking load of the coil body provided as Sample 2 were 43 times and 0.47 N-cm, respectively. The number of revolutions to breaking and breaking load of the coil body provided as Sample 3 were 55 times and 0.29 N-cm, respectively.

Figure 12:
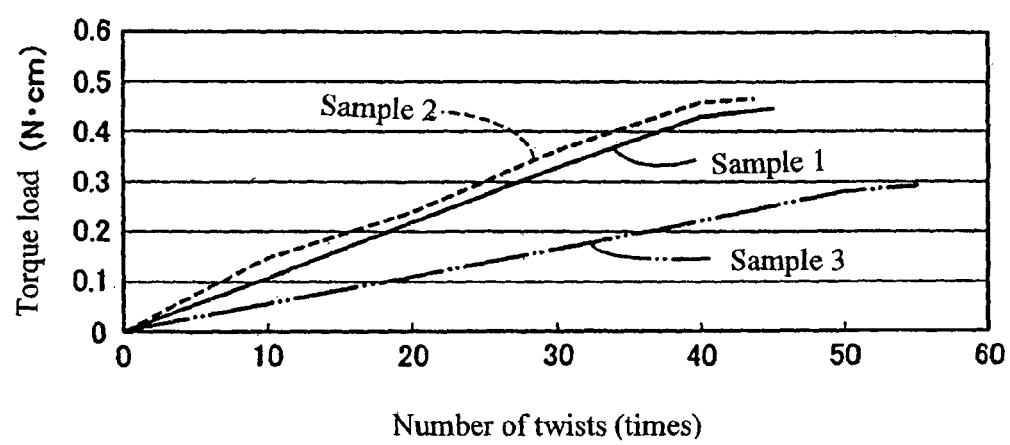
FIG. 12 is a graph showing the relationship of the number of times the coil body had been twisted and the torque load generated in the coil body, obtained from a torsion test conducted on one catheter coil body having a structure according to at least one embodiment of the present invention and two catheter coil bodies having a conventional structure and respectively made of wires of different diameters.

As shown in FIG. 12, the coil bodies provided by Samples 1 and 2, each made of thick wires with a diameter of 0.18 mm, clearly generated greater torque loads than the coil body provided as Sample 3, made of thin wires with a diameter of 0.15 mm, as a result of input of torsional force. In addition, there was no significant difference between the torque loads generated by the coil body provided as Sample 1 and coil body provided as Sample 2. From these results, it is easily understood that a coil body made of thicker wires provides better torque transmissibility than a coil body made of thinner wires. It is also acknowledged that torque transmissibility barely drops and is maintained favorably even when the distance between wires on one end of the coil body is increased through electro-polishing.

<Test 3>

First, three types of coil bodies having the same structures as the three coil bodies created in Test 2 were created and prepared (Samples 1 to 3). Then, a pure bend test and a tip buckling load test were conducted on the end of each coil body to examine the difference in flexibility, if any, between the end of the coil body provided as Sample 1 where a gap was formed between wires, and the ends of Samples 2 and 3 where substantially or nearly no gaps existed between wires.

The pure bend test was conducted on each coil body in the following manner. First, the base of the aforementioned end of each coil body was affixed via a torque gauge in a manner not allowing any movement, while the tip of the end was affixed to a moving chuck. Then, the moving chuck was moved to right and left along a curved path. This moved the end of each coil body by 90 degrees to right and left and thus caused the end to bend and deform. The maximum torque load reached in this test was measured with the torque gauge for each coil body. The results of this pure bend test are shown in FIG. 13.

On the other hand, the tip buckling load test was conducted in the following procedure. First, the aforementioned end of each of the coil bodies provided as Samples 1 to 3 was gripped at the base. In this condition, each coil was lowered vertically to cause the tip surface of the end of each coil body to be pressed against a load cell. In this condition, each coil body was further lowered until the coil body buckled. The load applied to the end of each coil body during this process was measured with the load cell and the maximum value was obtained. The results of this tip buckling load test are shown in FIG. 14.

Figure 13:
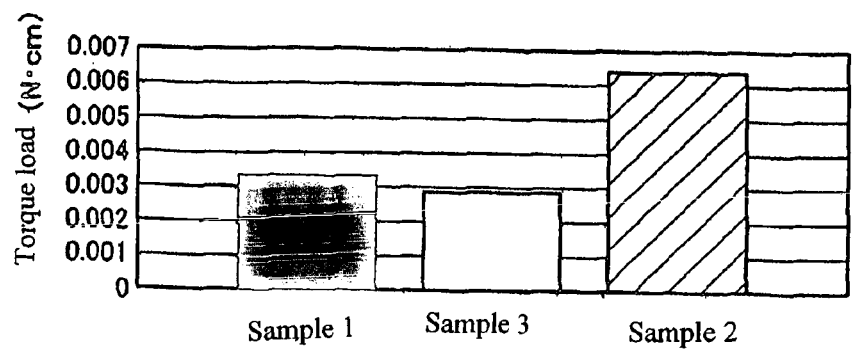
FIG. 13 is a graph showing the maximum torque load generated when the tip of the coil body was deformed by bending, obtained by conducting a pure bend test on each of the aforementioned three coil bodies.
Figure 14:
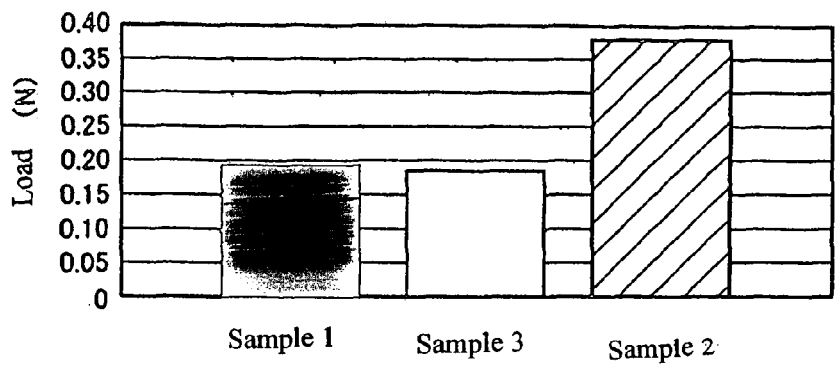
FIG. 14 is a graph showing the maximum torque load generated when the tip of the coil body was deformed by buckling, obtained by conducting a tip buckling load test on each of the aforementioned three coil bodies.

As shown in FIGS. 13 and 14, in both the pure bend test and tip buckling load test, the maximum torque loads or maximum loads measured on the coil bodies provided as Samples 1 and 3 were clearly smaller than the maximum torque load or maximum load measured on the coil body provided as Sample 2. In addition, there was no clear difference between the coil body provided as Sample 1 and the coil body provided as Sample 3 in either test. From these results, it is clearly acknowledged that even a coil body made of thicker wires can still exhibit excellent flexibility equivalent to a coil body made of thinner wires, if electro-polishing is provided to increase the distance between wires composing such coil body made of thicker wires.

<Test 4>

First, a coil body having the same structure as the one provided as Sample 1 in Test 2 was created and prepared (Sample 1). Separately, eight wires identical to the wires compsing the coil body provided as Sample 1 were stranded at a constant gradual pitch of 1.94 mm to create and prepare a coil body having a large gap between each pair of adjacent wires along the entire length of the coil body (Sample 4). Centerless grounding was also provided on one end of this coil body provided as Sample 4, in the same manner as with the coil body provided as Sample 1.

Next, a torsion test was conducted on the prepared coil bodies of Samples 1 and 4 in the same manner as in Test 2. The relationship of the number of times the coil body had been turned when the breaking occurred, and the corresponding torque load measured with the torque gauge, was checked for each coil body. The results are shown in FIG. 15.

Figure 15:
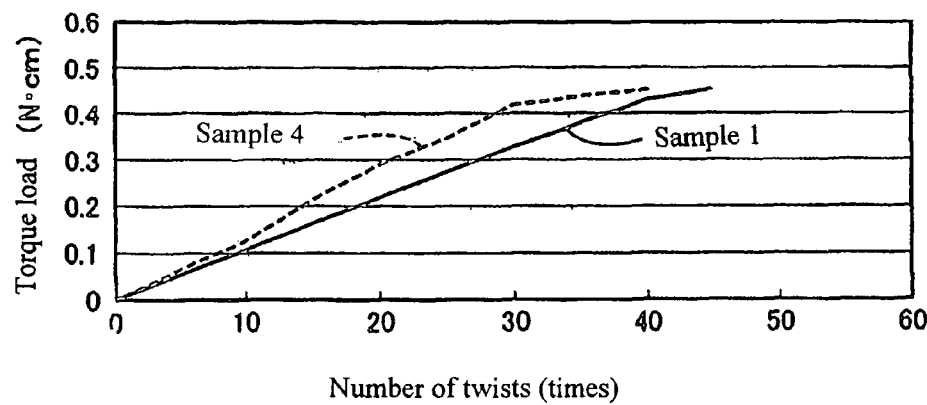
FIG. 15 is a graph showing the relationship of the number of times the coil body had been twisted and the torque load generated in the coil body, obtained by conducting a torsion test on a catheter coil body having a structure according to at least one embodiment of the present invention and a catheter coil body made with large gaps formed between wires along the entire length of the coil body.

As shown in FIG. 15, the coil body provided as Sample 4 had a breaking load of 0.46 N-cm after 40 revolutions. On the other hand, the breaking load of the coil body provided as Sample 1 did not reach 0.46 N-cm until the coil body had been twisted around 45 times. From this, it is easily acknowledged that excellent durability can be ensured when the distance between wires is increased only on one end.

The above described the specific structures of at least one embodiment of the present invention. It should be noted, however, that these structures are only examples and the present invention may not be at all limited to the above descriptions.

For example, the aforementioned embodiment used a wire having a circular lateral cross-section shape for wires (12). However, it is certainly possible to comprise wires (12) using a wire having a lateral cross-section shape other than circle.

It is also possible, for example, to form a coil body (10) by helically notching a long, thin metal pipe.

Furthermore, to form gaps (38) in the distal portion, a coil body (10) is formed by winding or stranding wires (12), then the distal portion (16) can be made of thinner wires (12) than the wires (10) composing the intermediate portion (18) or proximal portion (14), so that the gaps (38) are formed between the thinner wires (12) in the distal portion (16). In the case that a coil body (10) is formed by helically notching a metal pipe, the notch width in the distal portion (16) can be made larger than the notch width in the intermediate portion (18) or proximal portion (14), so that the gaps (38) are formed between the wires (12) in the distal portion (16).

In addition, the aforementioned embodiment gave a specific example of how the present invention can be applied to a catheter, and its production method, for dilating an occluded area formed in a cardiovascular vessel. It goes without saying, however, that the present invention can also be applied favorably to catheters that are inserted into the human body for the purpose of dilating an occluded area formed in blood vessels other than cardiovascular vessels, or for other purposes, as well as any production method for these catheters.

The present application claims priority to Japanese Patent Application No. 2004-369969, filed Dec. 21, 2004, the disclosure of which is incorporated herein by reference in its entirety.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A hollow catheter body configured to be inserted into a human body comprising:
   a coil body constituted by coils of a plurality of wires adjacent to one another wound or stranded in the same general direction, said coil body comprising a distal portion located at a front portion of the coil body with respect to a direction of insertion into the human body,
   a tip-tapered part provided in the distal portion, both an inner diameter and an outer diameter of the tip-tapered part are decreased toward a distal end of the distal portion, and
   a proximal portion located at a rear portion of the coil body with respect to the direction of insertion into the human body,
   wherein the coils of the coil body in the tip-tapered part have a reduced wire-thickness in an axial direction of the catheter body than the coils of the coil body in the proximal portion while the proximal portion and the distal portion of the coil body are prepared by winding or stranding the plurality of wires adjacent to one another at a constant pitch,
   wherein each distance Wd between the wires having the reduced wire-thickness adjacent to each other within the plurality of wires in the tip-tapered part is greater than each distance Wp between the wires adjacent to each other within the plurality of wires in the proximal portion, when seen in a cross section of the catheter body,
   wherein each wire in the tip-tapered part has a substantially semicircular cross sectional shape and is not in touch with the adjacent wire to form the distance Wd,
   wherein the plurality of wires in the proximal portion is formed by closely winding or stranding the plurality of wires to form the distance Wp.

2. The catheter body according to claim 1, wherein the distance Wd is about 8% to about 15% of a sum of the distance Wd and a width of one of the adjacent coils.

3. The catheter body according to claim 1, wherein a total of the distance Wd per pitch of the coils in the distal portion is about 8% to about 15% of the pitch.

4. The catheter body according to claim 1, wherein the distance Wp is substantially or nearly zero.

5. The catheter body according to claim 1, further comprising a tip portion affixed to the tip-tapered part of the distal portion of the coil body, wherein the tip portion is made of a radio-opaque material.

6. The catheter body according to claim 1, wherein the distance Wd is formed by electro-polishing of the distal portion of the coil body without substantially or nearly changing the pitch of the coils.

7. The catheter body according to claim 1, wherein the distal portion of the coil body has a surface, at least a portion of which is polished by centerless-grinding and has an outer diameter which is smaller than an outer diameter of the proximal portion.

8. The catheter body according to claim 1, wherein the coil body is composed of a single layer of the wires.

9. A catheter configured to be inserted into the human body, comprising: the catheter body of claim 1; a cover tube which covers the proximal portion of the catheter body; and a connector with which the proximal portion of the catheter body is coupled.

10. The catheter body according to claim 6, wherein the coil body has reduced stress by heat-treating of the coil body before the electro-polishing.

11. The catheter body according to claim 1, wherein the coils of the coil body in the rest of the distal portion other than the tip-tapered part have a reduced wire-thickness in the axial direction of the catheter body than the coils of the coil body in the proximal portion, and each distance between wires adjacent to each other in the rest of the distal portion is the distance Wd.

12. The catheter body according to claim 1, further comprising an intermediate portion located between the distal portion and the proximal portion, an outer diameter of the intermediate portion is reduced than an outer diameter of the proximal portion and larger than an outer diameter of the distal portion,
- wherein each wire in the proximal portion has a substantially circular cross sectional shape and is substantially touch with the adjacent wire to form the distance Wp, and
- each wire in the intermediate portion has a substantially semicircular cross sectional shape and is substantially touch with the adjacent wire to form the distance Wp.

13. The catheter body according to claim 12, wherein each outer surface of the distal portion and the intermediate portion is ground to form the wires having the substantially semicircular cross sectional shape.

14. The catheter body according to claim 1, wherein all of the coils having the reduced wire-thickness have substantially the same thickness.

15. The catheter body according to claim 1, wherein all of the coils of the coil body in the tip-tapered part have the reduced wire-thickness.

* * * * *